(12) United States Patent
Feinberg et al.

(10) Patent No.: US 9,086,403 B2
(45) Date of Patent: Jul. 21, 2015

(54) METHODS OF SCREENING FOR CELL PROLIFERATION OR NEOPLASTIC DISORDERS

(75) Inventors: Andrew P. Feinberg, Lutherville, MD (US); Christine A. Iacobuzio-Donahue, Ellicott City, MD (US); Dan L. Longo, Kensington, MD (US); Minoru Ko, Cockeysville, MD (US)

(73) Assignees: The Johns Hopkins University, Baltimore, MD (US); National Institutes of Health, Bethesda, MD (US)

( * ) Notice: Subject to any disclaimer, the term of this patent is extended or adjusted under 35 U.S.C. 154(b) by 956 days.

(21) Appl. No.: 11/145,331

(22) Filed: Jun. 3, 2005

(65) Prior Publication Data

US 2006/0003359 A1    Jan. 5, 2006

Related U.S. Application Data

(60) Provisional application No. 60/576,566, filed on Jun. 3, 2004, provisional application No. 60/646,296, filed on Jan. 24, 2005, provisional application No. 60/656,470, filed on Feb. 24, 2005.

(51) Int. Cl.
| | |
|---|---|
| *G01N 33/574* | (2006.01) |
| *G01N 33/53* | (2006.01) |
| *G01N 33/50* | (2006.01) |
| *C12Q 1/68* | (2006.01) |

(52) U.S. Cl.
CPC .......... *G01N 33/5017* (2013.01); *C12Q 1/6886* (2013.01); *G01N 33/5023* (2013.01); *G01N 33/574* (2013.01); *C12Q 2600/154* (2013.01)

(58) Field of Classification Search
None
See application file for complete search history.

(56) References Cited

U.S. PATENT DOCUMENTS

| | | |
|---|---|---|
| 2001/0007749 A1 | 7/2001 | Feinberg |
| 2002/0173036 A1 | 11/2002 | Carter |
| 2004/0002082 A1 | 1/2004 | Feinberg |
| 2004/0219559 A1 | 11/2004 | Feinberg |
| 2005/0048526 A1* | 3/2005 | Wang ................ 435/6 |

FOREIGN PATENT DOCUMENTS

WO    WO 2004/013316 A1    2/2004

OTHER PUBLICATIONS

Kaneda et al, Cancer Res, 2005, 65:11236-11240.*
Sakatani et al., Science, 2005, 307:1976-1978.*
Baker et al., BMJ, 2006, 332:1150-1152.*
Tockman et al., Cancer Res., 1992, 52:2711s-2718s.*
Carina, Nature, 2006, 442: 739-741.*
Ferrero et al., BMC Surg. 2003; 3: 1.*
Gryfe et al, Curr Probl Cancer, 1997, 21:234-299.*
Kang et al, Am J Surg Pathol, 1997, 21:417-423.*
Brittan et al, Gut, 2004, 6:899-910.*
Bowman et al., Cancer Res, 2001, 61:8408-8411.*
Staino-Coico, Cancer, 1989, 64:2579-2584.*
Schaid et al, Human Mol Genet, E pub Jan. 2004, 13:103-121.*
Christofori et al., "Deregulation of both imprinted and expressed alleles of the insulin-like growth factor 2 gene during β-cell tumorigenesis," *Nature Genetics*, vol. 10: pp. 196-201 (1995).
Cui et al., "Loss of IGF2 Imprinting: A Potential Marker of Colorectal Cancer Risk," *Science*, vol. 299: pp. 1753-1755 (2003).
Curtin and Snell, "Enzymic retrodifferentiation during hepatocarcinogenesis and liver regeneration in rats in vivo," *Br. J. Cancer*, vol. 48, No. 4: pp. 495-505 (1983).
Dittrich et al., "Imprint switching on human chromosome 15 may involve alternative transcripts of the SNRPN gene," *Natire Genetics*, vol. 14: pp. 163-170 (1996).
Feinberg et al. "Reduced Genomic 5-Methylcytosine Content in Human Colonic Neoplasia," *Cancer Research*, vol. 48: pp. 1159-1161 (1988).
Feinberg, Andrew P. "Genomic Imprinting and Cancer," *The Genetic Basis of Human Cancer*. pp. 43-55 (2002).
Feinberg, Andrew P., "Genomic imprinting and gene activation in cancer," *Nature Genetics*, vol. 4: pp. 110-113 (1993).
Feinberg, A. P. "Alterations in DNA Methylation in Colorectal Polyps and Cancer," *Basic and Clinical Perspectives of Colorectal Polyps and Cancer*. vol. 279: pp. 309-317 (1988).
Feinberg, Andrew P., "The epigenetics of cancer etiology," *Seminars in Cancer Biology*, vol. 14: pp. 427-432 (2004).
Haramis et al., "De Novo Crypt Formation and Juvenile Polyposis on BMP Inhibition in Mouse Intestine," *Science*, vol. 303: pp. 1684-1686 (2004).
Hassan and Howell, "Insulin-like Growth Factor II Supply Modifies Growth of Intestinal Adenoma in $Apc^{Min/+}$ Mice," *Cancer Research*, vol. 60: pp. 1070-1076 (2000).
Howe et al., "Twist is Up-Regulated in Response to Wnt1 and Inhibits Mouse Mammary Cell Differentiation," *Cancer Research*, Vo. 63: pp. 1906-1913 (2003).
Kaneko et al., "Musashi1: An Evolutionally Conserved Marker for CNS Progenitor Cells Including Neural Stem Cells," *Developmental Neuroscience*, vol. 22: pp. 139-153 (2000).
Kitsberg et al., "Allele-specific replication timing of imprinted gene regions," *Nature*, vol. 364: pp. 459-463 (1993).
Kuroiwa et al., "Peg3 imprinted gene on proximal chromosome 7 encodes for a zinc finger protein," *Nature Genetics*, vol. 12: pp. 186-190 (1996).
LaSalle and Lalande, "Homologous Association of Oppositely Imprinted Chromosomal Domains," *Science*, vol. 272: pp. 725-728 (1996).
Leighton et al., "Disruption of imprinting caused by deletion of the H19 gene region in mice," *Nature*, vol. 375: pp. 34-39 (1995).

(Continued)

*Primary Examiner* — Mark Halvorson
(74) *Attorney, Agent, or Firm* — DLA Piper LLP (US)

(57) ABSTRACT

The invention relates to methods and compositions for identifying subjects having, or predisposed to having, a neoplastic or cell proliferation or neoplastic disorder. The methods are applicable to any type of tissue sample and can be conducted on otherwise normal tissue.

18 Claims, 10 Drawing Sheets

(56) References Cited

OTHER PUBLICATIONS

Lipkin and Deschner, "Early Proliferative Changes in Intestinal Cells," *Cancer Research*, vol. 36: pp. 2665-2668 (1976).

Nagai et al., "Cloning of No t I-Cleaved Genomic DNA Fragments Appearing as Spots in 2D Gel Electrophoresis," *Biochemical and Biophysical Research Communications*, vol. 213, No. 1: pp. 258-265 (1995).

Pant et al., "The nucleotides responsible for the direct physical contact between the chromatin insulator protein CTCF and the H19 imprinting control region manifest parent of origin-specific long-distance insulation and methylation-free domains," *Genes & Development*, vol. 17: pp. 586-590 (2003).

Potten et al., "Identification of a putative intestinal stem cell and early lineage marker; musashi-1," *Differentiation*, vol. 71: pp. 28-41 (2003).

Ravenel et al., "Loss of Imprinting of Insulin-Like Growth Factor-II (IGF2) Gene in Distinguishing Specific Biologic Subtypes of Wilms Tumor,"*Journal of the National Cancer Institute*, vol. 93, No. 22: pp. 1698-1703 (2001).

Ripoche et al., "Deletion of the H19 transcription unit reveals the existence of a putative imprinting control element," *Genes & Development*, vol. 11: pp. 1596-1604 (1997).

Sell and Pierce, "Maturation Arrest of Stem Cell Differentiation is a Common Pathway for the Cellular Origin of Teratocarcinomas and Epithelial Cancers," *Laboratory Investigation*, vol. 70, No. 1: pp. 6-22 (1994).

Su et al., "Multiple Intestinal Neoplasia Caused by a Mutation in the Murine Homolog of the APC Gene," *Science*, vol. 256: pp. 668-670 (1992).

Tartof and Henikoff, "Trans-Sensing Effects from *Drosophila* to Humans," *Cell*, vol. 65: pp. 201-203 (1991).

Taunton et al., "A Mammalian Histone Deacetylase Related to the Yeast Transcriptional Regulator Rpd3p," *Science*, vol. 272: pp. 408-411 (1996).

Thiery and Morgan, "Breast cancer progression with a Twist," *Nature Medicine*, vol. 10, No. 8: pp. 777-778 (2004).

Torrance et al., "Combinatorial chemoprevention of intestinal neoplasia," *Nature Medicine*, vol. 6, No. 8: pp. 1024-1028 (2000).

Velcich et al., "Colorectal Cancer in Mice Genetically Deficient in the Mucin Muc2," *Science*, vol. 295: pp. 1726-1729 (2002).

Vu and Hoffman, "Promoter-specific imprinting of the human insulin-like growth factor-II gene," *Nature*, vol. 371: pp. 714-717 (1994).

Walters et al., "Transcriptional enhancers act in *cis* to suppress position-effect variegation," *Genes & Development*, vol. 10: pp. 185-195 (1996).

West et al., "Localization of Villin, a Cytoskeletal Protein Specific to Microvilli, in Human Ileum and Colon and in Colonic Neoplasms," *Gastroenterology*, vol. 94: pp. 343-352 (1988).

van de Wetering et al., "The β-Catenin/TCF-4 Complex Imposes a Crypt Progenitor Phenotype on Colorectal Cancer Cells," *Cell*, vol. 111: pp. 241-250 (2002).

Woodson et al., "Loss of Insulin-Like Growth Factor-II Imprinting and the Presence of Screen-Detected Colorectal Adenomas in Women,"*Journal of the National Cancer Institute*, vol. 96, No. 5: pp. 407-410 (2004).

Yang et al., "Targeted Inactivation of $p27^{kip1}$ is Sufficient for Large and Small Intestinal Tumorigenesis in the Mouse, Which Can Be Augmented by a Western-Style High-Risk Diet," *Cancer Research*, vol. 63: pp. 4990-4996 (2003).

Cui et al., "Loss of Imprinting in Colorectal Cancer Linked to Hypomethylation of *H19* and *IGF2*", *Cancer Research*, 62:6442-6446 (2002).

Fabian et al., "Short-Term Breast Cancer Prediction by Random Periareolar Fine-Needle Aspiration Cytology and the Gail Risk Model", *Journal of the National Cancer Institute*, 92(15): 1217-1227 (2000).

Lieberman, R., "Prostate Cancer Chemoprevention: Strategies for Designing Efficient Clinical Trials", *Urology*, 57(Suppl 4A):224-229 (2001).

Paller et al., "Z-4',5'-didehydro-5'-deoxy-5'-fluoroadenosine (MDL 28,842), an irreversible inhibitor of S-adenosylhomocysteine hydrolase, suppresses proliferation of cultured keratinocytes and squamous carcinoma cell lines", *Cancer Res.*, 53(24):6058-6060 (1993).

Ransohoff D.F., "Cancer. Developing molecular biomarkers for cancer", Science, 299(5613):1679-1680 (2003).

Barlow et al., "The mouse insulin-like growth factor type-2 receptor is imprinted and closely linked to the *Tme* locus," *Nature*, vol. 349: pp. 84-87 (1991).

Batlle et al., "β-Catenin and TCF Mediate Cell Positioning in the Intestinal Epithelium by Controlling the Expression of EphB/EphrinB," *Cell*, vol. 111: pp. 251-263 (2002).

Beckwith et al., "Nephrogenic Rests, Nephroblastomatosis, and the Pathogenesis of Wilms' Tumor," *Pediatric Pathology*, vol. 10, Nos. 1-2: pp. 1-36 (1990).

Bennett et al., "Structural-proliferative units and organ growth: effects of insulin-like growth factor 2 on the growth of colon and skin," *Development*, vol. 130: pp. 1079-1088 (2003).

Borkowski et al., "Anterior-posterior subdivision and the diversification of the mesoderm in *Drosophila*," *Development*, vol. 121: pp. 4183-4193 (1995).

Brachmann et al., "The *SIR2* gene family, conserved from bacteria to humans, functions in silencing, cell cycle progression, and chromosome stability," *Genes & Development*, vol. 9: pp. 2888-2902 (1995).

Brownell et al., "Tetrahymena Histone Acetyltransferase A: A Homolog to Yeast Gcn5p Linking Histone Acetylation to Gene Activation," *Cell*, vol. 84: pp. 843-851 (1996).

\* cited by examiner

A H19 Deletion Model

B H19 DMR Mutation Model

C Experiments

| Model | Age | Tumor | Histology |
|---|---|---|---|
| Deletion | 42 days | + | + |
| | 120 days | + | + |
| Mutation | 150 days | n.d. | + |

# METHODS OF SCREENING FOR CELL PROLIFERATION OR NEOPLASTIC DISORDERS

CROSS REFERENCE TO RELATED APPLICATIONS

This application claims the benefit of priority under 35 U.S.C. §19(e) of U.S. Ser. No. 60/576,566, filed Jun. 3, 2004, U.S. Ser. No. 60/646,296, filed Jan. 24, 2005, and U.S. Ser. No. 60/656,470, filed Feb. 24, 2005, the entire contents of which are incorporated herein by reference.

STATEMENT AS TO FEDERALLY SPONSORED RESEARCH

The inventions were made with Government support under R01CA65145 and K08CA106610 awarded by the National Institutes of Health. The Government has certain rights in the inventions.

BACKGROUND INFORMATION

1. Field of the Invention

This invention relates generally to screening for risk or or presence of neoplastic disorders, and more particularly to screening for biomarkers present in a biological sample obtained from a subject that are indicative of a predisposition for a neoplastic (e.g., benign or malignant) or cell proliferative disorder.

2. Background Information

Each mammalian cell carries two copies of each gene, one inherited from the mother (on the maternal chromosome) and one inherited from the father (on the paternal chromosome). Most of the autosomal genes and X-linked genes in females are therefore biallelic i.e. both paternal and maternal alleles of the gene are expressed and the information of both copies is actively used in protein synthesis. However, in humans and other mammals, monoallelic expression of biallelic genes has been demonstrated. Allelic exclusion can result from two different mechanisms. The first mechanism is independent of the parental origin. The second mechanism, called genomic imprinting, is an epigenetic modification of a specific parental chromosome in the gamete or zygote that leads to monoallelic or differential expression of the two alleles of a gene in somatic cells of the offspring. Imprinting affects various essential cellular and developmental processes, including intercellular signaling, RNA processing, cell cycle control, and promotion or inhibition of cellular division and growth.

Imprinted genes can show monoallelic expression in some tissues and biallelic expression in others. For example, the insulin-like growth factor II gene (IGF2) is imprinted in most tissues but is biallelic in brain and monoallelically expressed in liver. Loss of imprinting (LOI) of the IGF2 gene, or activation of the normally silent maternally inherited allele, occurs in many common cancers (Feinberg, A., Semin. Cancer Biol. 14, 427 (2004)). The term LOI simply means loss of preferential parental origin-specific gene expression and can involve either abnormal expression of the normally silent allele, leading to biallelic expression, or silencing of the normally expressed allele, leading to epigenetic silencing of the locus. About 10% of the population shows LOI of IGF2, and this molecular trait is associated with a personal and/or family history of colorectal neoplasia (Cui et al., Science 299, 1753 (2003); Woodson et al., J. Natl. Cancer. Inst. 96, 407 (2004)). Imprinting of IGF2 is regulated by a differentially methylated region (DMR) upstream of the nearby untranslated H19 gene. Deletion of the DMR leads to biallelic expression (LOI) of IGF2 in the offspring when the deletion is maternally inherited (Leighton, et al., Nature 375, 34 (1995); Ripoche, et al., Genes Dev. 11, 1596 (1997)). Thus, abnormal imprinting in cancer can lead to activation of normally silent alleles of growth-promoting genes.

Currently, no single biochemical marker, or plurality of biochemical markers, reliably identifies a subject at risk for developing a disease associated with LOI and/or uncontrolled cell proliferation or neoplastic disorders (e.g., benign and cancer). Thus, there exists a need for diagnostic methods and compositions that can utilize cell differentiation information to identify those individuals at risk for developing a cell proliferation or neoplastic disorder. Such information can optionally be correlated with abnormal gene expression resulting from epigenetic alterations in the genome of a subject. Early implementation of a prophylactic therapy and periodic screening can lead to prevention of such a disorder.

SUMMARY

The present invention is based on the discovery that alterations in ratios of differentiated and undifferentiated cell populations can be used as early indicators for the risk of developing cell proliferation or neoplastic disorders. In general, the invention features methods of determining a subject's risk of developing a cell proliferation or neoplastic disorders, such as cancer, by obtaining a biological sample, such as from blood or intestinal tissue, from a subject and determining the level of cell differentiation in the same or a different tissue. Optionally, this information can be correlated with an alteration in the expression of a target gene. An alteration in expression of a target gene can directly or indirectly result from a loss of imprinting of a target gene.

In one embodiment, a method of determining predisposition of a subject to developing a cell proliferation or neoplastic disorder is provided. The method includes determining the ratio of undifferentiated to differentiated cells in a normal biological sample from the subject. The ratio of undifferentiated to differentiated cells, as compared to a reference ratio, is indicative of a predisposition for developing a cell proliferation or neoplastic disorder. Optionally, the method further includes identifying cells displaying abnormal expression of at least one target gene in the same or different biological sample from the subject. A target gene includes any gene the expression of which is affected by loss of imprinting. For example, the expression of the H19 gene or IGF2 gene is directly affected by their imprinting status. However, the expression of an IFG2-related gene, such as IgfIR, IRS-1, IRS-2, PI3K, Akt, p70S6 kinase, FOXO, GSK3, MDM2, mTOR, Cyclin D1, c-Myc, Shc, Grb2, SOS, Ras, Raf, MEK, Erk, or MAPK gene, is indirectly affected by the imprinting status of H19 and/or IGF2. Thus, the expression of IGF2-related genes can be stimulated by a loss of imprinting of, for example, the IGF2 gene. In general, methods of the invention include analyzing the biological sample for a change in the expression of a target gene that is directly or indirectly associated with loss of imprinting, or a polymorphism thereof. Loss of imprinting can result from, for example, a change in the methylation status of the gene. The change in methylation status can be hypomethylation of, for example, a differentially methylated region (DMR) of the H19 gene and/or a DMR of the IGF2 gene. Subsequently, a reference ratio can be generated from tissue obtained from a subject that includes cells displaying normal imprinting of at least one of the H19 gene and the IGF2 gene.

In another embodiment, determining the ratio of undifferentiated to differentiated cells in the sample includes identifying a biomarker associated with a differentiated or undifferentiated cell. The biomarker can include, but is not limited to, Shh (Sonic hedgehog), Tcf4, Lef1, Twist, EphB2, EphB3, Hes1, Notch1, Hoxa9, Dkk1, T1e6, Tcf3, Bmi1, Kit, Musashi1 (Msi1), Cdx1, Hes5, Oct4, Ki-67, β-catenin, Noggin, BMP4, PTEN (phosphorylated PTEN), Akt (phosphorylated Akt), Villin, Aminopeptidase N (anpep), Sucrase isomaltase (SI), Ephrin-B1 (EfnB1), Cdx2, Crip, Apoa1, Aldh1b1, Calb3, Dgat1, Dgat2, Clu, Hephaestin, Gas1, Ihh (Indian hedgehog), Intrinsic factor B12 receptor, IFABP, or KLF4.

In another embodiment, determining the ratio of undifferentiated to differentiated cells in the sample can include: a) imaging the sample using immunohistochemical identification of biomarker molecules specifically associated with a differentiated or undifferentiated cell population; b) imaging the sample using standard microscopy and distinguishing differentiated from undifferentiated cells using morphologic measurements; c) imaging the sample using immunohistochemical identification of proliferation antigens and their distribution within colonic crypts; or d) imaging the sample using immunoflourescent identification of molecules specific to a biomarker associated with a differentiated or undifferentiated cell population. Nucleic acid analyses can also be performed, for example, e) measuring RNA levels; f) measuring gene expression; g) whole genome expression analyses; or allele specific expression.

In some embodiments, the cells can be epithelial cells obtained from, for example, a rectal "Pap" test (e.g., a scraped sample). In alternative embodiments, the epithelial cells can be obtained from intestinal tissue, such as, for example, the colon. In other embodiments, the cells can be obtained from the lumen of the intestinal tissue. In other embodiments, the cells can be obtained from the crypts of the lumen. The cell proliferation or neoplastic disorder can be associated with a solid tumor such as, for example, an adenoma.

The methods of the invention encompass screening tissue from subjects not previously known to have a cell proliferation or neoplastic disorder, such as a neoplasm of the colon. For example, the results of the methods provided herein can be correlated with the subject's family genetic history. In addition, the subject can be subjected to additional tests including, but not limited to, chest X-rays, colorectal examinations, endoscopic examination, MRI, CAT scanning, gallium scanning, and barium imaging.

In other embodiments, methods of determining whether a subject is predisposed to developing a cell proliferation or neoplastic disorder include obtaining a biological sample from a subject and contacting the sample with an array of immobilized biomolecules that specifically interact with a biomarker indicative of a differentiated or undifferentiated cell. The methods further include obtaining a subject profile by detecting a modification of the biomolecules that is indicative of the ratio of differentiated to undifferentiated cells in the sample. The subject profile can be compared with a reference profile that includes one or more values, each value representing the level of biomarker in a reference sample obtained from one or more reference subjects displaying normal imprinting of the target gene. In some embodiments, the biomolecules can be proteins, such as antibodies (e.g., monoclonal antibodies). In other embodiments the biomolecules can be antigens or receptors. Optionally, the method further includes identifying cells displaying abnormal expression of at least one target gene in the same or different biological sample from the subject.

In another embodiment, diagnostic kits for detecting a cell proliferation or neoplastic disorder, or a predisposition to a cell proliferation or neoplastic disorder, are provided. Such kits can include an array for detecting a biomarker indicative of a differentiated or undifferentiated cells in a sample obtained from a subject. The array can include a substrate having a plurality of addresses, each address having disposed thereon an immobilized biomolecule, wherein each biomolecule individually detects a biomarker indicative of a differentiated or undifferentiated cells. Optionally, the kit can include a means for identifying abnormal imprinting of at least one target gene in the biological sample.

In another embodiment, methods of determining whether a therapy regimen is effective for preventing or inhibiting a cell proliferation or neoplastic disorder are provided. Such methods include identifying a subject that is predisposed to developing a cell proliferation or neoplastic disorder and administering to the subject a therapy that inhibits or prevents an increase in the number of undifferentiated cells in a target tissue of the subject. The methods further include contacting a biological sample comprising non-neoplastic cells from the subject with an array of immobilized biomolecules that specifically interact with a biomarker indicative of a differentiated or undifferentiated cell and obtaining a subject profile by detecting a modification of the biomolecules, wherein the modification is indicative of the ratio of differentiated to undifferentiated cells in the sample. The subject profile can be compared with a reference profile that includes one or more values, each value representing the level of biomarker in a reference sample obtained from one or more reference subjects displaying normal imprinting of the target gene. Such theranostic methods can include providing the determination to a caregiver and altering the therapy based upon the determination.

In other embodiments, methods of preparing an undifferentiated cell are provided. Such methods include contacting a more committed cell with an agent that causes the more committed cell to dedifferentiate into an undifferentiated cell, wherein the agent affects the imprinting of at least one of the H19 gene and the IGF2 gene. The committed cells can be normal or cancer cells. In some embodiments, the committed cells are differentiated cells.

In other embodiments, methods of producing an altered cell population comprising undifferentiated cells capable of being recommitted into more differentiated cells, are provided. Such methods include contacting an initial cell population comprising committed cells with an agent that modulates the imprinting status of a target gene in a cell derived from epithelial tissue, culturing the cells, and identifying the cells undifferentiated cells or recovering the undifferentiated cells from the altered cell population. Such cells can be recovered a biomarker as described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Figure 1:
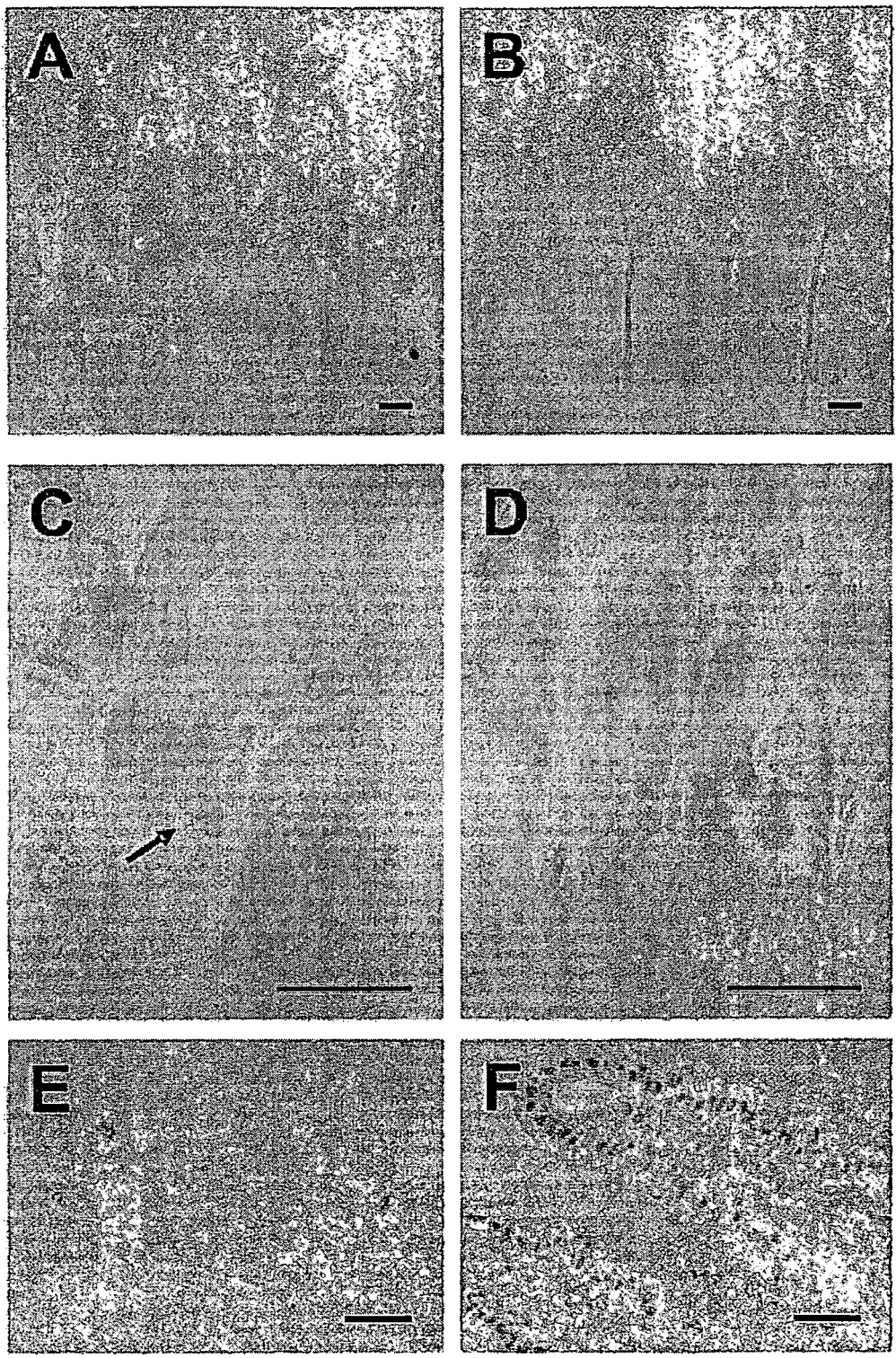
FIG. 1, panels A-F, depict immunohistochemical analysis of villin and musashi1 in 120 day old LOI(−) and LOI(+) mice.

Other features and advantages of the invention will be apparent from the following detailed description, and from the claims.

DETAILED DESCRIPTION

Methods and compositions for detecting a modification in the ratio of differentiated and undifferentiated cells in a biological sample from a subject are provided. Such modifications may result from epigenetic alterations that 1) shift normal tissue to a more undifferentiated state; 2) increase the target cell population for subsequent genetic alterations; or 3) act independently in tumor initiation. Thus, the methods of the invention allow for determining a change in the balance or ratio of undifferentiated to differentiated cells in the sample.

The present invention has many embodiments and relies on many patents, applications and other references for details known to those of the art. Therefore, when a patent, application, or other reference is cited or repeated below, it should be understood that it is incorporated by reference in its entirety for all purposes as well as for the proposition that is recited. For example, methods and compositions for detecting a loss of imprinting (LOI) indicative of an increased risk of developing cancer are disclosed in U.S. Pat. App. Pub. No. 20040219559 (application Ser. No. 10/629,318), U.S. Pat. App. Pub. No. 20040002082 (application Ser. No. 10/336, 552), and U.S. Pat. App. Pub. No. 20010007749 (application Ser. No. 10/759,917), each of which also is hereby incorporated by reference in its entirety for all purposes.

As used in this application, the singular form "a," "an," and "the" include plural references unless the context clearly dictates otherwise. For example, the term "an agent" includes a plurality of agents, including mixtures thereof.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry $3^{rd}$ Ed., W. H. Freeman Pub., New York, N.Y. and Berg et al. (2002) Biochemistry, $5^{th}$ Ed., W. H. Freeman Pub., New York, N.Y., all of which are herein incorporated in their entirety by reference for all purposes.

In addition to their use to identify subjects who are at risk, the new methods can be used as a routine screen or "prescreen" for subjects that may have a family genetic history of cancer, such as colon cancer or pancreatic cancer. The methods can also identify those subjects who are not currently at risk for developing cancer, thus avoiding the need for additional testing.

"Genomic imprinting" or "allelic exclusion according to parent of origin" is a mechanism of gene regulation by which only one of the parental copies of a gene is expressed. Paternal imprinting means that an allele inherited from the father is not expressed in offspring. Maternal imprinting means that an allele inherited from the mother is not expressed in offspring. Imprinted genes are the genes for which one of the parental alleles is repressed whereas the other one is transcribed and expressed. The expression of an imprinted gene may vary in different tissues or at different developmental stages. Imprinted genes may be expressed in a variety of tissue or cell types such as muscle, liver, spleen, lung, central nervous system, kidney, testis, ovary, pancreas, placenta, skin, adrenal, parathyroid, bladder, breast, pituitary, intestinal, salivary gland blood cells, lymph node and other known in art. For instance, IGF2 imprinting results in repression of the maternally-derived allele in most tissues except brain, adult liver and chondrocytes (Vu T. H. and Hoffman A. R. (1994) Nature, 371:714-717).

Genomic imprinting has been implicated in cell proliferation or neoplastic disorders such as cancer. For example, loss of heterozygosity (LOH) in the childhood Wilms tumor (WT) occurs on chromosome 11. Examination of RNA from Wilms tumor led to a discovery that not one but both IGF2 alleles were expressed in 70% of Wilms tumors. In addition, in 30% of cases, both alleles of H19 were expressed. In contrast, examination of RNA from normal tissue shows normal imprinting with the expression of one allele of IGF2 and H19. The term for this novel genetic alteration is loss of imprinting (LOI) which simply means loss of preferential parental origin-specific gene expression and can involve either abnormal expression of the normally silent allele, leading to biallelic expression, or silencing of the normally expressed allele, leading to epigenetic silencing of the locus. Thus, abnormal imprinting in cancer can lead to activation of normally silent alleles of growth-promoting genes.

DNA methylation plays a role in the control of genomic imprinting. First, some imprinted genes in mice, such as H19, show parental origin-specific, tissue-independent methylation of CpG islands. This methylation represents imprinting on the paternal chromosome and is not secondary to changes in gene expression. Second, knockout mice deficient in DNA methyltransferase, and exhibiting widespread genomic hypomethylation, do not show allele-specific methylation of the H19 CpG island and exhibit biallelic expression of H19 and loss of expression of IGF2. Similar parental origin-specific methylation has also been observed for a CpG island in the first intron of the maternally inherited, expressed allele of the IGF2 receptor gene (IGF2R). Methyltransferase deficient knockout mice show loss of methylation of IGF2R and epigenetic silencing of the gene.

Widespread alterations in DNA methylation in human tumors were discovered years ago (Feinberg, A P. (1993) Nature Genet. 4:110-113) and remain the most commonly found alteration in human cancers. These alterations are ubiquitous to both benign and malignant neoplasms. Both decreased and increased methylation have been found at specific sites in tumors, with an overall decrease in quantitative DNA methylation (Feinberg et al. (1988) Cancer Res. 48:1159-1161; Feinberg, A. P. (1988) Prog. Clin. Biol. Res. 79:309-317).

In humans, as in mice, the paternal allele of a CpG island in the H19 gene and its promoter is normally methylated, and the maternal allele is unmethylated. Because tumors with LOI of IGF2 showed reduced expression of H19, the methylation pattern of H19 has been examined in tumors with LOI. In all cases showing LOI of IGF2, the H19 promoter exhibits 90%-100% methylation at the sites normally unmethylated on the maternally inherited allele. Thus, the maternal allele has acquired a paternal pattern of methylation, consistent with observed expression of IGF2 on the same maternally derived chromosome in these tumors. In contrast, tumors without LOI of IGF2 show no change in the methylation of H19, indicating that these changes are related to abnormal imprinting and not malignancy per se. The same alterations in methylation of the maternal allele of H19 are found in patients with Beckwith-Wiedemann syndrome (BWS) having LOI of IGF2. BWS is a disorder of prenatal overgrowth and cancer, transmitted as an autosomal dominant trait, or arising sporadically.

Another mechanism by which LOI may act involves disruption of an imprinting control center on chromosome 11, similar to that recently described for the BWS/AS region of chromosome 15 (Dittrich et al. (1996) Nat. Genet. 14: 163-170). Thus, disruption of a gene spanning this region could cause abnormal imprinting, as well as BWS and/or cancer, at least when inherited through the germline.

Another mechanism for LOI involves loss of trans-acting factors which may establish and maintain a normal pattern of genomic imprinting once such a pattern is established in the germline. Trans-acting modifiers of imprinting are likely to exist, since imprinting of transgenes is host strain-dependent. Such genes may thus act as tumor suppressor genes in humans and other species.

Yet another mechanism of imprinting that may be disrupted in cancer involves histone deacetylation which is linked to X-inactivation in mammals and to telomere silencing in yeast. Genes for both histone acetylase and histone deacetylase have recently been isolated (Brownell et al. (1996) Cell 84:843-851 Taunton et al. (1996) Science 272: 408-411). In addition, telomere silencing in yeast also involves the action of specific genes, e.g., SIR1-SIR4, some of which have homologues in mammals (Brachmann et al. (1995) Genes Develop. 9:2888-2902). Similarly, some examples of gene silencing in mammals may resemble position-effect variation in *Drosophila*, a form of position-dependent epigenetic silencing (Walters et al. (1996) Genes Develop. 10:185-195). Finally, imprinted loci on maternal and paternal chromosomes may interact during DNA replication. Chromosomal regions harboring imprinted genes show replication and timing asynchrony (Kitsberg et al. (1993) Nature 364:459-463). Furthermore, the two parental homologues of some imprinted genes show nonrandom proximity in late S-phase (LaSalle. J. M. and Lalande, M. (1996) Science 272:725-728), indicating a form of chromosomal cross-talk, as has been observed for epigenetic silencing in Drosophila (Tartoff, K. D. and Henikoff, S. (1991) Cell 65:201-203). The human IGF2 and H19 genes are normally imprinted, i.e., show preferential expression of a specific parental allele. Some tumors undergo loss of imprinting (LOI) in cancer, with one or more of the following: biallelic expression of IGF2, epigenetic silencing of H19; and/or abnormal expression of the paternal H19 allele, and this observation has been extended to a wide variety of childhood and adult malignancies. Normal imprinting can be maintained in part by allele-specific, tissue-independent methylation of H19, since LOI is associated with abnormal methylation of the normally unmethylated maternal H19 allele.

Methods of Identifying At-Risk Subjects

In one embodiment, methods of determining predisposition of a subject to developing a cell proliferation or neoplastic disorder are provided. In general, the subject is a human. The methods include determining the ratio of undifferentiated to differentiated cells in a sample obtained from a subject and generating a subject profile. The ratio of undifferentiated to differentiated cells, as compared to a reference ratio or reference profile, is indicative of a predisposition for developing a cell proliferation or neoplastic disorder. Optionally, the methods include identifying cells displaying abnormal imprinting of at least one target gene in the normal biological sample from the subject, or cells displaying increased levels of IGF2 gene expression.

"Target gene," as used herein, includes any genomic sequence the expression of which is altered, directly or indirectly, by genomic imprinting. A change in genomic imprinting can include loss of imprinting. For example, the expression of the H19 gene or IGF2 gene is directly affected by their imprinting status. However, the expression of an IFG2-related gene, such as IgflR, IRS-1, IRS-2, PI3K, Akt, p70S6 kinase, FOXO, GSK3, MDM2, mTOR, Cyclin D1, c-Myc, Shc, Grb2, SOS, Ras, Raf, MEK, Erk, or MAPK gene, is indirectly affected by the imprinting status of H19 and/or IGF2. Thus, the expression of IGF2-related genes can be stimulated by a loss of imprinting of, for example, the IGF2 gene. In general, methods of the invention include analyzing the biological sample for a change in the expression of a target gene that is directly or indirectly associated with loss of imprinting, or a polymorphism thereof. Loss of imprinting can result from, for example, a change in the methylation status of the gene. The change in methylation status can be hypomethylation of, for example, a DMR of the H19 gene and/or a DMR of the IGF2 gene. Subsequently, a reference ratio can be generated from tissue obtained from a subject that includes cells displaying normal imprinting of at least one of the H19 gene and the IGF2 gene.

Methods provided herein may include analyzing the biological sample for a change in methylation of a target gene, or a polymorphism thereof. The change in methylation can be hypomethylation of, for example, a DMR of the H19 gene and a DMR of the IGF2 gene. However, it is understood that any change in DNA methylation, histone modification such as, but not limited to, acetylation, methylation, phosphorylation, or any change in allele-specific gene expression can result in the over or under expression of a target gene, thereby affecting the differentiation status of a cell or group of cells in a tissue. In addition, any change in the expression of genes that are indicators of progenitor cell fraction, such as musashi and twist, is also encompassed by methods provided herein.

Methods provided herein may include analyzing genomic DNA from a sample and detecting altered expression of a target gene resulting directly or indirectly from altered loss of imprinting (LOI) of, for example, the IGF2 or the H19 gene.

It is understood that LOI can directly or indirectly affect the expression of a target gene. For example, the expression of IGF2-related genes, such as IgfIR, IRS-1, IRS-2, PI3K, Akt, p70S6 kinase, FOXO, GSK3, MDM2, mTOR, Cyclin D1, c-Myc, Shc, Grb2, SOS, Ras, Raf, MEK, Erk, and MAPK, is affected by the imprinting status of IGF2. Exemplary methods of detecting DNA methylation include Southern blotting, bisulfite sequencing, methylation-specific PCR (MSP), real-time MSP, In situ MSP, immunofluorescent staining, and HPLC. Exemplary methods of detecting histone modification include ChIP analysis. Exemplary methods for detecting mRNA include real-time RT-PCR, northern blotting and In situ hybridization. Exemplary methods for detecting protein include Immunohistochemical staining, Immunofluorescent staining and western blotting.

Methods provided herein may further include generating a ratio or "subject profile" from tissue obtained from a subject that includes cells displaying normal expression of a target gene such as, for example, the H19 gene and/or the IGF2 gene. A "subject profile," as used herein, simply means identifying the ratio of undifferentiated and differentiated cells in a given sample from test subject. A ratio can be generated from a sample taken from, for example, intestinal tissue. The subject profile can be expressed as an array "signature" or "pattern" of specific identifiable biomarkers that distinguish undifferentiated cells from differentiated cells. The array signature can be color-coded as in for easy visual or computer-aided identification. The signature can also be described as a number(s) that correspond to values attributed to the biomarkers identified by the array. "Array analysis," as used herein, is the process of extrapolating information from an array using statistical calculations such as factor analysis or principle component analysis (PCA). In addition to being expressed as a signature, a reference ratio can be expressed as a "threshold" value or series of threshold values. For example, a single threshold value can be determined for the level of a particular biomarker, or series of biomarkers, in a particular sample. A threshold value can have a single value or a plurality of values, each value representing a level of a specific biomarker, or specific series of biomarkers that are indicative of the presence of differentiated or undifferentiated cells.

The ratio constituting the subject profile can be compared to a "reference ratio" or "reference profile." In general, reference profiles are generated from a series of different subjects and tissues. The reference profile is used as a baseline for determining whether the ratio provided in the subject profile is normal or abnormal for the subject and/or type of tissue being tested. "Subject profiles" and "reference profiles" are discussed below.

The biological sample used to generate a reference ratio can be same or different from the sample used to identify abnormal imprinting of a target gene. As used herein, biological sample includes any tissue sample, such as intestinal tissue, blood, or serum. It is understood that the subject from which the sample is obtained need not have a cell proliferation or neoplastic disorder, such as colon cancer or pancreatic cancer, in order for the methods of the invention to be useful. In fact, the invention contemplates the use of normal (i.e., non-neoplastic) tissue in order to identify a subject predisposed to developing a cell proliferation or neoplastic disorder. The biological sample can include epithelial cells obtained from, for example, a rectal Pap test. The biological sample can include cells obtained from intestinal tissue, such as the colon or pancreas. More specifically, the cells can be obtained from the lumen of the intestinal tissue. Such cells can be, for example, epithelial cells obtained from the crypts of the lumen of the intestinal tissue. A cell proliferation or neoplastic disorder can be associated with a solid tumor, such as an adenoma. The results of a screen for a predisposition to developing a cell proliferation or neoplastic disorder can be correlated with the subject's family genetic history. Subsequently, the subject can undergo additional diagnostic tests including chest X-rays, colorectal examinations, endoscopic examination, MRI, CAT scanning, gallium scanning, and barium imaging.

In other embodiments, cell differentiation can be determined by more conventional means, such as microscopy and immunohistochemical identification. For example, a sample can be imaged using immunohistochemical identification of biomarkers specifically associated with a differentiated or undifferentiated cell population. In addition, standard microscopy can be used distinguish differentiated from undifferentiated cells using morphologic measurements. Further, immunohistochemical identification of proliferation antigens and their distribution within, for example, colonic crypts, can be used to distinguish differentiated from undifferentiated cells. Finally, the sample can be imaged using immunoflourescent identification of molecules specific to a biomarker associated with a differentiated or undifferentiated cell population.

In addition, "normal" (i.e., non-cancerous) tissue obtained from a subject can be examined for other characteristics indicative of a predisposition for developing a cell proliferation or neoplastic disorder such as cancer. Such characteristics can include changes in the expression of genes or expression of proteins that are associated with specific niches (and size of the niche) or compartment of a particular tissue. Also included are changes in distribution of cells within niches or compartments from normal tissue. Also included are changes in the distribution and number of progenitor cells in such tissues. Also included are increases in the number of stem cells and/or precursor cells for cancer in the tissue. Further, an increase in the number of cells showing cancer-like features can be used as an indicator of increased risk of developing cancer. Similarly, an alteration in the maturation of the otherwise normal cells can be indicative of a cell proliferation or neoplastic disorder.

A "biomarker" can be a molecule that distinguishes differentiated from undifferentiated cells. Such biomarkers include, but are not limited to, Shh (Sonic hedgehog), Tcf4, Lef1, Twist, EphB2, EphB3, Hes1, Notch1, Hoxa9, Dkk1, T1e6, Tcf3, Bmi1, Kit, Musashi1 (Msi1), Cdx1, Hes5, Oct4, Ki-67, β-catenin, Noggin, BMP4, PTEN (phosphorylated PTEN), and Akt (phosphorylated Akt) for identifying undifferentiated cells. Biomarkers useful for identifying differentiated cells include, but are not limited to, Villin, Aminopeptidase N (anpep), Sucrase isomaltase (SI), Ephrin-B1 (EfnB1), Cdx2, Crip, Apoa1, Aldh1b1, Calb3, Dgat1, Dgat2, Clu, Hephaestin, Gas1, Ihh (Indian hedgehog), intrinsic factor B12 receptor, IFABP, and KLF4. A biomarker can further encompass oligosaccharides, polysaccharides, oligopeptides, proteins, oligonucleotides, and polynucleotides. Oligonucleotides and polynucleotides include, for example, DNA and RNA, e.g., in the form of aptamers. A biomarker can also include organic compounds, organometallic compounds, salts of organic and organometallic compounds, saccharides, amino acids, and nucleotides, lipids, carbohydrates, drugs, steroids, lectins, vitamins, minerals, metabolites, cofactors, and coenzymes.

Various antigens are associated with undifferentiated and differentiated cells. The term "associated" here means the cells expressing or capable of expressing, or presenting or capable of being induced to present, or comprising, the respective antigen(s). Each specific antigen associated with an undifferentiated cell or a differentiated cell can act as a biomarker. Hence, different types of cells can be distinguished from each other on the basis of their associated particular antigen(s) or on the basis of a particular combination of associated antigens.

The methods provided herein may utilize, in part, various means for distinguishing less differentiated cells from those that have undergone differentiation. Cell differentiation is a process whereby structures and functions of cells are progressively committed to give rise to more specialized cells. Therefore, as the cells become more committed, they become more specialized. In the majority of mammalian cell types, cell differentiation is a one-way process leading ultimately to terminally differentiated cells. However, although some cell types persist throughout life without dividing and without being replaced, many cell types do continue to divide during the lifetime of the organism and undergo renewal. This may be by simple division (e.g. liver cells) or, as in the case of cells such as haemopoietic cells and epidermal cells, by division of relatively undifferentiated stem cells followed by commitment of one of the daughter cells to a program of subsequent irreversible differentiation. All of these processes, however, have one feature in common: cells either maintain their state of differentiation or become more differentiated. They do not become undifferentiated or even less differentiated.

The methods provided herein can also encompass identification of those cells that may have undergone "dedifferentiation." Dedifferentiation is a process whereby structures and functions of cells are progressively changed to give rise to less specialized cells. Some cells naturally undergo limited reverse differentiation (dedifferentiation) in vivo in response to tissue damage. For example, liver cells have been observed to revert to an enzyme expression pattern similar to the fetal enzyme pattern during liver regeneration (Curtin and Snell, 1983, Br. J. Cancer, Vol 48; 495-505). While preserving the entire information encoded on its genome, cells undergoing retrodifferentiation lose morphological and functional complexity by virtue of a process of self-deletion of cytoplasmic structures and the transition to a more juvenile pattern of gene expression. This results in a progressive uniformization of originally distinct cell phenotypes and to a decrease of responsiveness to regulatory signals operational in adult cells.

In another embodiment, methods of determining whether a subject is predisposed to developing a cell proliferation or neoplastic disorder may include identifying a subject comprising cells displaying increased levels of, for example, IGF2 gene expression. Subsequently or in parallel, the ratio of undifferentiated to differentiated cells in the same or different sample from the subject can be determined. The determination of increased levels of, for example, IGF2 gene expression can include detection of increased levels of IGF2 mRNA and/or IGF2 polypeptide. Methods of detecting mRNA and/or polypeptides in a sample are well known to those skilled in the art of molecular biology. It is understood that increased levels of the target gene expression includes increased levels of target gene mRNA and/or increased levels of a polypeptide encoded by the target gene, such as H19, IGF2, IgflR, IRS-1, IRS-2, PI3K, Akt, p70S6 kinase, FOXO, GSK3, MDM2, mTOR, Cyclin D1, c-Myc, Shc, Grb2, SOS, Ras, Raf, MEK, Erk, or MAPK gene.

In another embodiment, a method of determining whether a subject is predisposed to developing a cell proliferation or neoplastic disorder, is provided. The method may include contacting a normal biological sample from a subject with an array of immobilized biomolecules that specifically interact with a biomarker indicative of a differentiated or undifferentiated cells. The method may further include obtaining a subject profile by detecting a modification of the biomolecules. The modification of a biomolecule may be indicative of the ratio of differentiated to undifferentiated cells in the sample. "Biomolecules," as used herein, include proteins, such as monoclonal or polyclonal antibodies. Biomolecules also include antigens or receptors. Modification, as used herein, may include binding Shh, Tcf4, Lef1, Twist, EphB2, EphB3, Hes1, Notch1, Hoxa9, Dkk1, Tle6, Tcf3, Bmi1, Kit, Musashi1 (Msi1), Cdx1, Hes5, Oct4, Ki-67, □-catenin, Noggin, BMP4, PTEN (phosphorylated PTEN), Akt (phosphorylated Akt), Villin, Aminopeptidase N (anpep), Sucrase isomaltase (SI), Ephrin-B1 (EfnB1), Cdx2, Crip, Apoa1, Aldh1b1, Calb3, Dgat1, Dgat2, Clu, Hephaestin, Gas1, Ihh (Indian hedgehog), Intrinsic factor B12 receptor, IFABP, or KLF4 to a biomolecule.

Subsequently, the subject profile may be compared with a reference profile that comprises one or more values. Each value can represent the level of biomarker in a reference sample obtained from one or more reference subjects that are not predisposed to developing a cell proliferation or neoplastic disorder. The method may further include identifying abnormal expression of at least one target gene in the same or different biological sample obtained from the subject. Exemplary target genes include H19, IGF2, IgflR, IRS-1, IRS-2, PI3K, Akt, p70S6 kinase, FOXO, GSK3, MDM2, mTOR, Cyclin D1, c-Myc, Shc, Grb2, SOS, Ras, Raf, MEK, Erk, or MAPK gene. The abnormal expression of the target gene may be directly or indirectly related to a loss of imprinting.

The presence or absence of LOI may be detected by examining any condition, state, or phenomenon which causes LOI or is the result of LOI. Such conditions, states, and phenomena include, but are not limited to 1) causes of LOI, such as the state or condition of the cellular machinery for DNA methylation, the state of the imprinting control region on chromosome 11, the presence of trans-acting modifiers of imprinting, the degree or presence of histone deacetylation; 2) state of the genomic DNA associated with the genes or gene for which LOI is being assessed, such as the degree of DNA methylation; and 3) effects of LOI, such as: a) relative transcription of the two alleles of the genes or gene for which LOI is being assessed; b) post-transcriptional effects associated with the differential expression of the two alleles of the genes or gene for which LOI is being assessed; c) relative translational of the two alleles of the genes or gene for which LOI is being assessed; d) post-translational effects associated with the differential expression of the two alleles of the genes or gene for which LOI is being assessed; e) other downstream effects of LOI, such as altered gene expression measured at the RNA level, at the splicing level, or at the protein level or post-translational level (i.e., measure one or more of these properties of an imprinted gene's manifestation into various macromolecules); changes in function that could involve, for example, cell cycle, signal transduction, ion channels, membrane potential, cell division, or others (i.e., measure the biological consequences of a specific imprinted gene being normally or not normally imprinted (for example, QT interval of the heart). Another group of macromolecular changes could be in associated processes such as histone acetylation, histone deacetylation, or RNA splicing.

When detecting the presence or absence of LOI by relying on any one of these conditions, states, or phenomena, it is possible to use a number of different specific analytical techniques. In particular, it is possible to use any of the methods for determining the pattern of imprinting known in the art. It is recognized that the methods may vary depending on the gene to be analyzed.

Conditions, states, and phenomena which may cause LOI and may be examined to assess the presence or absence of LOI include: the state or condition of the cellular machinery for DNA methylation, the state of the imprinting control region on chromosome 11, the presence of trans-acting modifiers of imprinting, the degree or presence of histone deacetylation or histone deacetylation, imprinting control center, transacting modulatory factors, changes in chromatin caused by polycomb-like proteins, trithorax-like proteins, human homologues of other chromatin-affecting proteins in other species such as Su(var) proteins in Drosophila, SIR proteins in yeast, mating type silencing in yeast, XIST-like genes in mammals.

It is also possible to detect LOI by examining the DNA associated with the gene or genes for which the presence or absence of LOI is being assessed. By the term "the DNA associated with the gene or genes for which the presence or absence of LOI is being assessed" it is meant the gene, the DNA near the gene, or the DNA at some distance from the gene (as much as a megabase or more away, i.e., methylation changes can be far away, since they act on chromatin over long distances). Such approaches include measuring the degree of methylation in the DNA associated with the gene or genes for which the presence or absence of LOI is being assessed. It is also possible to detect LOI by examining modifications to DNA-associated protein, such as histone acetylation and histone deacetylation; changes to binding proteins detected by band shift, protection assays, or other assays, in addition to changes to the DNA sequence itself.

The degree of methylation in the DNA, associated with the gene or genes for which the presence or absence of LOI is being assessed, may be measured by means of a number of analytical techniques. For example, the DNA, associated with the gene or genes for which the presence or absence of LOI is being assessed, may be sequenced using conventional DNA sequencing techniques as described in "Current Protocols in Molecular Biology" (Asubel et al., Wiley Interscience, 1998). In this case, the biological sample will be any which contains sufficient DNA to permit sequencing.

In addition, the degree of methylation in the DNA, associated with the gene or genes for which the presence or absence of LOI is being assessed, may be measured by fluorescent in situ hybridization (FISH) by means of probes which identify and differentiate between genomic DNAs, associated with the gene for which the presence or absence of LOI is being assessed, which exhibit different degrees of DNA methylation. In this case, the biological sample will typically be any which contains sufficient whole cells or nuclei to perform short term culture, Usually, the sample will be a tissue sample which contains 10 to 10,000, preferably 100 to 10,000, whole somatic cells.

Typically, in methods for assaying allele-specific gene expression which rely upon the differential transcription of the two alleles, RNA is reverse transcribed with reverse transcriptase, and then PCR is performed with PCR primers that span a site within an exon where that site is polymorphic (i.e., normally variable in the population), and this analysis is performed on an individual that is heterozygous (i.e., informative) for the polymorphism. One then uses any of a number of detection schemes to determine whether one or both alleles is expressed. See also, Rainier et al. (1993) Nature 362:747-749; which teaches the assessment of allele-specific expression of IGF2 and H19 by reverse transcribing RNA and amplifying cDNA by PCR using new primers that permit a single round rather than nested PCR; Matsuoka et al. (1996) Proc. Natl. Acad Sci USA 93:3026-3030 which teaches the identification of a transcribed polymorphism in p57.sup.KIP2; Thompson et al. (1996) Cancer Research 56:5723-5727 which teaches determination of mRNA levels by RPA and RT-PCR analysis of allele-specific expression of p57.sup.KIP2; and Lee et al. (1997) Nature Genet. 15:181185 which teaches RT-PCR SSCP analysis of two polymorphic sites. Such disclosures are herein incorporated by reference. In this case, the biological sample will be any which contains sufficient RNA to permit amplification and subsequent reverse transcription followed by polymerase chain reaction. Typically, the biological sample will be a tissue sample which contains Ito 10,000,000, preferably 1000 to 10,000,000, more preferably 1,000,000 to 10,000,000, somatic cells.

It is also possible to utilize allele specific RNA-associated in situ hybridization (ASISH) to detect the presence or absence of LOI by relying upon the differential transcription of the two alleles. In ASISH, the relative abundance of transcribed mRNA for two alleles is assessed by means of probes which identify and differentiate between the mRNA transcribed from the two alleles. Typically, the probes are tagged with fluorescent labels which results in a high sensitivity and easily quantifiable results. ASISH is described in Adam et al. (1996) "Allele-specific in situ hybridization (ASISH) analysis: a novel technique which resolves differential allelic usage of H19 within the same cell lineage during human placental development," Development 122:83-47, which is incorporated herein by reference. In this case, the biological sample will typically be any which contains sufficient whole cells or nuclei to perform histological section and in situ hybridization. Usually, the sample will be a tissue sample which contains 10-100,000, preferably 100-1000, whole somatic cells.

Accordingly, it is also possible to detect LOI by examining allele-specific post-transcriptional effects (i.e., effects after transcription and before translation), like alternate splicing that depends on which allele was transcribed, and detection of secondary structure of the RNA.

It is also possible to detect LOI by examining the relative translation of the two alleles of the gene or genes for which the presence or absence of LOI is being measured. In this case, the presence or relative abundance of the two polypeptides arising from the expression of the two alleles is measured directly. This approach can be effected by any known technique for detecting or quantifying the presence of a polypeptide in a biological sample. For example, allele-specific translational effects may be examined by quantifying the proteins expressed by the two alleles using antibodies specific for each allele (transcribed, translated polymorphism). Such effects may be measured and/or detected by such analytical techniques as Western blotting, or use of an ELISA assay. In this case, the biological sample will be any which contains a sufficient amount of the polypeptide(s) encoded by the gene(s) for which the presence or absence of LOI is being measured.

LOI may also be detected by examining post-translational effects, such as secondary modifications that are specific to one allele, like glycosylation or phosphorylation. For example, one allele may be modified, say by phosphorylation or glycosylation, and the other one not. Because the polymorphism encodes a recognition motif, then one can readily distinguish the difference by a Western blot, detecting alternate migration of the polypeptide or protein; use of antibodies specific for the modified form; radioactive incorporation of phosphoryl group or glycosyl group or other modification (i.e., in living cells, followed by the detection of a band at a varying location).

LOI may also be detected by reliance on other allele-specific downstream effects. For example, depending on the metabolic pathway in which lies the product of the imprinted gene; the difference will be 2× versus 1× (or some number in between) of the product, and therefore the function or a variation in function specific to one of the alleles. For example, for IGF2, increased mitogenic signaling at the IGFI receptor, increased occupancy of the IGF1 receptor increased activity at the IGF2 catabolic receptor, decreased apoptosis due to the dose of IGF2; for KvLQT1, change in the length of the QT interval depending on the amount and isoform of protein, or change in electrical potential, or change in activity when the RNA is extracted and introduced into Xenopus oocytes.

It is also possible to detect LOI by detecting an associated halotype, i.e., linked polymorphisms that identify people whose genes are prone to LOI. Thus, LOI may be detected by relying on a polymorphism, i.e., a genetic difference between the two alleles. However, it will be recognized that many of the techniques described above may be used to detect LOI even when there is no polymorphism in the two alleles of the gene or genes for which the presence or absence of LOI is being measured. For example, LOI may be detected by reliance on allele-specific DNA methylation (polymorphism independent); histone acetylation; other modifications to DNA; or alterations in replication timing, when the imprinted allele shows "replication timing asynchrony" i.e. the two alleles replicate at different times. When the two alleles replicate at the same time, LOI may be detected by FISH. Since imprinted alleles pair in the late S phase, LOI may be detected by the absence of such pairing in the late S as observed by FISH.

On the other hand certain techniques are more conveniently used when there is a polymorphism in the two alleles of the gene or genes for which the presence or absence of LOI is being measured. For example, RT-PCR followed by SSCP (single strand conformational polymorphism) analysis; restriction enzyme digestion analysis followed by electrophoresis or Southern hybridization; or radioisotopic PCR; PCR; allele-specific oligonucleotide hybridization; direct sequencing manually or with an automated sequencer; denaturing gradient gel electrophoresis (DGGE); and many other analytical techniques can be used to detect LOI when relying on a polymorphism.

The presence or absence of LOI may be determined for any gene or genes which are known to normally exhibit imprinting. Currently there are about 22 genes which are known to be normally imprinted (see Feinberg in The Genetic Basis of Human Cancer, B Vogelstein & K Kinzler, Eds., McGraw Hill, 1997, which is incorporated herein by reference). Examples of such genes include, but are not limited to, IGF2, H19, p57$_{KIP2}$, KvLQT1, TSSC3, TSSCS, and ASCL2. However, it is expected that additional genes which normally exhibit imprinting will be discovered in the future and the LOI of such genes may be the target of the present methods and are therefore included in the present invention.

Direct approaches to identifying novel imprinted genes include, but are not limited to, positional cloning efforts aimed at identifying imprinted genes near other known imprinted genes (Barlow et al. (1991) Nature 349:84-87); techniques comparing gene expression in parthenogenetic embryos to that of normal embryos (Kuroiwa et al. (1996) Nat. Genet. 12:186-190) and restriction landmark genome scanning (Nagai et al. (1995) Biochem. Biophys. Res. Commun. 213:258-265).

The methods described herein encompass the identification of subjects predisposed to developing a cell proliferation or neoplastic disorder by determining the ratio of non-cancerous undifferentiated cells to that of non-cancerous differentiated cells in a tissue sample obtained from the subject. It should be understood that the present methods of assessing the risk of contracting cancer may include comparing the ratio described above against one or more predetermined threshold values, such that, if the ratio is below a given threshold value then the subject is assigned to a low risk population for developing a cell proliferation or neoplastic disorder. Alternatively, the analytical technique may be designed not to yield an explicit numerical value for the ratio of non-cancerous undifferentiated cells to that of non-cancerous differentiated cells, but instead yield only a first type of signal when the ratio is below a threshold value and/or a second type of signal when the ratio is above a threshold value. It is also possible to carry out the present methods by means of a test in which the ratio is signaled by means of a non-numeric spectrum such as a range of colors encountered with immunohistochemical analysis of a tissue sample. The present methods may optionally include detecting LOI in the tissue.

The present methods of assessing the risk of developing a cell proliferative disorder may suitably be carried out on any subject selected from the population as a whole. However, it may be preferred to carry out this method on certain selected groups of the general population when screening for the predisposition to particular types of cancer. Preferably, the present method is used to screen selected groups which are already known to have an increased risk of contracting the particular type of cancer in question.

The methods described herein encompass the identification of subjects predisposed to developing a cell proliferation or neoplastic disorder by determining the ratio of non-cancerous undifferentiated cells to that of non-cancerous differentiated cells in a tissue sample obtained from the subject. These methods optionally include detecting LOI in the tissue by determining, for example, the degree of methylation of the genomic DNA associated with particular target gene(s) for which LOI is being detected.

Exemplary epigenetic alterations in human cancers include global DNA hypomethylation, gene hypomethylation and promoter hypermethylation, and loss of imprinting (LOI) of the insulin-like growth factor-II gene (IGF2). One mechanism for LOI is hypermethylation of a differentially methylated region (DMR) upstream of, for example, the H19 gene, allowing activation of the normally silent maternal allele of IGF2. Another mechanism for LOI includes hypomethylation of the H19 DMR as well as the DMR upstream of exon 3 of IGF2 in colorectal cancers. This hypomethylation has been identified in both colorectal cancers and normal mucosa from the same patients, and in cell lines with somatic cell knockout of DNA methyltransferases DNMT1 and DNMT3B. Thus, hypermethylation and hypomethylation are mechanisms for LOI. For example, hypomethylation of both the IGF2 gene and the H19 gene can be correlated with loss of imprinting of the IGF2 gene and LOI of IGF2 can be correlated with the presence and increased risk for developing cancer, e.g., colorectal cancer.

Methods of the present invention may optionally include analyzing LOI of, for example, the IGF2 gene by analyzing hypomethylation of the IGF2 gene or H19 gene, to identify an increased risk of developing cancer in a subject. This information may be correlated with cell differentiation/undifferentiation data obtained from the same subject. The method may include analyzing a biological sample from the subject for hypomethylation of a differentially methylated region (DMR) of the H19 gene and/or the IGF2 gene, or a polymorphism and/or fragment of the H19 DMR and/or IGF2 DMR. The H19 DMR, or fragment thereof, may include a CTCF binding site, for example, CTCF binding site 1 or CTCF binding site 6.

In certain aspects, the subject is an apparently normal subject. Hypomethylation can be analyzed in a DNA region corresponding to an H19 DMR. An IGF2 DMR sequence can correspond to GenBank nucleotides 631-859 (accession no. Y13633). One exemplary IGF2 DMR corresponds to position −566 bp to −311 bp relative to exon 3 of IGF2 (i.e., nucleotides 661 to 916 of GenBank accession no. Y13633. Another DMR of H19 corresponds to nucleotides 2057 to 8070 of Genbank accession no. AF087017, incorporated herein by reference in its entirety; which correspond in variant form to nucleotides 3829 to 9842 of AF125183. In certain aspects the method comprises analyzing the biological sample for hypomethylation of positions within the region of the H19 DMR that are analyzed using the nested primer pairs SEQ ID NOs:21 and 22, followed by SEQ ID NOs:23 and 24. Furthermore, in certain aspects, hypomethylation is analyzed in a DNA region corresponding to an IGF2 DMR. In certain aspects the method comprises analyzing the biological sample for hypomethylation of positions within the region of the IGF2 DMR that are analyzed using the nested primer pairs SEQ ID NOs:1 and 2, followed by SEQ ID NOs:3 and 4, or the region analyzed using primer pairs SEQ ID NOs: 29 and 30, followed by SEQ ID NOs:27 and 28.

Thus, in addition to including devices and reagents for distinguishing differentiated from undifferentiated cells, a kit for performing methods of the invention can further include a plurality of oligonucleotide probes, primers, or primer pairs, or combinations thereof, capable of binding to the DMR of IGF2 or H19 with or without prior bisulfite treatment of the DMR. The kit can include an oligonucleotide primer pair that hybridizes under stringent conditions to all or a portion of the DMR only after bisulfite treatment. The kit can include instructions on using kit components to identify an increased risk of developing cancer. In certain embodiments the instructions are directed at subjects of the general population. The kit for example, includes one or both of a primer pair corresponding to the primer pair SEQ ID NO:21 and SEQ ID NO:22 and the primer pair SEQ ID NO: 23 and SEQ ID NO:24. In another aspect, the kit for example, includes one or both of a primer pair corresponding to the primer pair SEQ ID NO:25 and SEQ ID NO:26, and the primer pair SEQ ID NO: 27 and SEQ ID NO:28.

Hypomethylation of a DMR is present when there is a measurable decrease in methylation of the DMR. Methods for determining methylation states are provided herein. For example, the H19 DMR can be determined to be hypomethylated when it is methylated at less than 10, less than 5, or less than 3 sites of all of the greater than 25 methylation sites within the H19 DMR. Alternatively, as illustrated in the Examples provided herein, hypomethylation of the H19 DMR can be identified when less than 50% or less than 75% of the methylation sites analyzed are not methylated. Methylation state can be analyzed for these DMRs by analyzing less than all of the methylation sites within the DMR. In certain aspects, the methylation sites are those sites for IGF2 that are located within the fragments amplified by the nested primer pairs SEQ ID NO:1 and SEQ ID NO:2 followed by SEQ ID NO:3 and SEQ ID NO:4, or SEQ ID NO:25 and SEQ ID NO:26 followed by SEQ ID NO:27 and SEQ ID NO:28. For H19, in certain aspects methylation sites of fragments of the present invention are those found within nested primer pairs SEQ ID NO:21 and SEQ ID NO:22 followed by SEQ ID NO:23 and SEQ ID NO:24.

A fragment of the H19 DMR or IGF2 DMR can be the region of the H19 DMR or IGF2 DMR that is amplified and/or flanked by primers that correspond to SEQ ID NOS:1-4 and 5-32. For example, the fragment of the H19 DMR can be the region of the H19 DMR that is amplified by the primer pair recited in SEQ ID NOS:21 and 22, or the primer pair recited in SEQ ID NOS:23 and 24, or by the nesting of SEQ ID NOS:21 and 22 followed by SEQ ID NOS:23 and 24. As another example, the fragment of the IGF2 DMR can be the region of the IGF2 DMR that is amplified by the primer pair recited in SEQ ID NOS: 25 and 26, or the primer pair recited in SEQ ID NOS:27 and 28, or by the nesting of SEQ ID NOS:25 and 26 followed by SEQ ID NOS:27 and 28. As another example, the fragment of the IGF2 DMR can be the region of the IGF2 DMR that is amplified by the primer pair recited in SEQ ID NOS: 1 and 2, or the primer pair recited in SEQ ID NOs:3 and 4, or by the nesting of SEQ ID NOS:1 and 2 followed by SEQ ID NOs:3 and 4. The sequences of the exemplary primers are listed below:

| | |
|---|---|
| 5' GGTGAGGATGGGTTTTTGTT 3' | (SEQ ID NO: 1) |
| 5' CTACTCTCCCAACCTCCCTAA 3' | (SEQ ID NO: 2) |
| 5' ATTGGGGGTGGAGGGTGTAT 3' | (SEQ ID NO: 3) |
| 5' TCTATTACACCCTAAACCCAA 3' | (SEQ ID NO: 4) |
| 5' ATCTTGCTGACCTCACCAAGG 3' | (SEQ ID NO: 5) |
| 5' CGATACGAAGACGTGGTGTGG 3' | (SEQ ID NO: 6) |
| 5' CCGACTAAGGACAGCCCCCAAA 3' | (SEQ ID NO: 7) |
| 5' TGGAAGTCTCTGCTCTCCTGTC 3' | (SEQ ID NO: 8) |
| 5'-ACAGTGTTCCTGGAGTCTCGCT 3' | (SEQ ID NO: 9) |
| 5' CACTTCCGATTCCACAGCTACA 3' | (SEQ ID NO: 10) |
| 5' ACAGGGTCTCTGGCAGGCTCAA 3' | (SEQ ID NO: 11) |
| 5' ATGAGTGTCCTATTCCCAGATG 3' | (SEQ ID NO: 12) |
| 5' AACTGGGGTTCGCCCGTGGAA 3' | (SEQ ID NO: 13) |
| 5' CAAATTCACCTCTCCACGTGC 3' | (SEQ ID NO: 14) |
| 5' GATCCTGATGGGGTTAGGATGT 3' | (SEQ ID NO: 15) |
| 5' GGAATTTCCATGGCATGAAAAT 3' | (SEQ ID NO: 16) |
| 5' GGTCTGCCTTGGTCTCCTAACT 3' | (SEQ ID NO: 17) |
| 5' GGCCACTTTCCTGTCTGAAGAC 3' | (SEQ ID NO: 18) |
| 5' CAGTCTCCACTCCACTCCCAAC 3' | (SEQ ID NO: 19) |
| 5' GACCTCTCCCTCCCAGACCACT 3' | (SEQ ID NO: 20) |
| 5'-GAGTTTGGGGGTTTTTGTATAGTAT-3' | (SEQ ID NO: 21) |
| 5' CTTAAATCCCAAACCATAACACTA-3' | (SEQ ID NO: 22) |
| 5' GTATATGGGTATTTTTGGAGGT-3' | (SEQ ID NO: 23) |
| 5' CCATAACACTAAAACCCTCAA-3' | (SEQ ID NO: 24) |
| 5'-GGGAATGTTTATTTATGTATGAAG-3' | (SEQ ID NO: 25) |
| 5' TAAAAACCTCCTCCACCTCC-3' | (SEQ ID NO: 26) |
| 5' TAATTTATTTAGGGTGGTGTT-3' | (SEQ ID NO: 27) |
| 5' TCCAAACACCCCCACCTTAA-3' | (SEQ ID NO: 28) |
| 5' GTATAGGTATTTTTGGAGGTTTTTTA 3' | (SEQ ID NO: 29) |
| 5' CCTAAAATAAATCAAACACATAACCC 3' | (SEQ ID NO: 30) |
| 5' GAGGTTTTTTATTTTAGTTTTGG-3' | (SEQ ID NO: 31) |
| 5' ACTATAATATATAAACCTACAC 3' | (SEQ ID NO: 32) |

Embodiments of the present invention are based on the finding of an association between a change in the ratio of undifferentiated to differentiated cells in a sample. This change may optionally be correlated with a loss of imprinting (LOI) of the IGF2 gene and family history of colorectal cancer (CRC). Accordingly, the present invention relates to a method for identifying an increased risk of developing cancer in a subject. The method includes analyzing a biological sample from the subject for a change in the ration of undifferentiated to differentiated cells in a sample. Such a change can be indicative of an increased risk of developing cancer. Certain embodiments of the invention may further include analyzing genomic DNA for altered methylation of the IGF2 gene or the H19 gene. The method for example, includes analyzing genomic DNA from the sample for hypomethylation of the IGF2 gene or the H19 gene.

A method according to the present invention can be performed during routine clinical care, for example as part of a general regular checkup, on a subject having no apparent or suspected neoplasm such as cancer. Therefore, the present invention in certain embodiments, provides a screening method for the general population. The methods of the present invention can be performed at a younger age than present cancer screening assays, for example where the method can be performed on a subject under 65, 55, 50, 40, 35, 30, 25, or 20 years of age.

If the biological sample of the subject in question is found to exhibit a change in the ratio of undifferentiated to differentiated cells in the same or different sample from the subject as compared to a reference ratio, then that subject is identified as having an increased probability of having cancer. In these embodiments, further diagnostic tests may be carried out to probe for the possibility of cancer being present in the subject. Examples of such further diagnostic tests include, but are not limited to, chest X-ray, carcinoembryonic antigen (CEA) or prostate specific antigen (PSA) level determination, colorectal examination, endoscopic examination, MRI, CAT scanning, or other imaging such as gallium scanning, and barium imaging. Furthermore, the method of the invention can be coincident with routine sigmoidoscopy/colonoscopy of the subject. The method could involve use of a very thin tube, or a digital exam to obtain a colorectal sample. Additional diagnostic tests for LOI of specific genes can be performed.

According to the present invention, the biological or tissue sample can be drawn from any tissue that is susceptible to cancer. For example, the tissue may be obtained by surgery, biopsy, swab, stool, or other collection method. The biological sample for methods of the present invention can be, for example, a sample from colorectal tissue, or in certain embodiments, can be a blood sample, or a fraction of a blood sample such as a peripheral blood lymphocyte (PBL) fraction. Methods for isolating PBLs from whole blood are well known in the art. An example of such a method is provided in the Example section herein. In addition, it is possible to use a blood sample and enrich the small amount of circulating cells from a tissue of interest, e.g., colon, breast, etc. using a method known in the art.

An exemplary method of screening a subject for a predisposition to colon cancer may include scraping an area associated with the large intestine with a spatula similar to the techniques used to obtain cells for a Pap smear. The scraped cells may then be smeared onto a slide, fixed with compounds suitable for distinguishing undifferentiated cells from differentiated cells, and subsequently analyzed under a microscope. Image analysis technology has been developed which may fully automate this process.

Alternatively, the cells obtained from scrape specimen may be introduced into a liquid based transport medium having properties suitable for maintaining the cells in solution while allowing for the detection of biomarkers associated with the undifferentiated/differentiated state of the cells. For example, the transport medium may include any combination of the following: 1) a fixative that helps retain cellular morphology and allow cells to retain the ability to be analyzed for biomarkers by molecular methods; 2) an isotonic osmolarity medium to maintain cellular volumetric integrity; 3) a mucolytic agent to disrupt mucous; 4) a blood lysing agent such as ammonium chloride or acidic acid; 5) a cellular preservative; 6) a cellular ion agent to break up groups of, for example, colon cells so that they can be analysized individually; 7) an anticoagulant such as heparin sodium; and/or 8) a stain to allow for cellular detection.

Once prepared and contacted with compounds suitable for detecting biomarker(s) that facilitate distinguishing undifferentiated from differentiated cells, the specimen may be analyzed via flow cytometry technology. Flow cytometry is a process by which cells pass singly in a fluid stream. The exact methods of achieving this may vary. It may be achieved by suspending the cells in isotonic fluid medium and introducing it into a nozzle shaped chamber with a small exit diameter. The ratio of undifferentiated to differentiated cells can be compared against, for example, a threshold value as described above. Biomarkers which may be used to distinguish undifferentiated cells from differentiated cells are discussed elsewhere in this disclosure. This method can optionally be coupled with detecting LOI in the tissue obtained from the subject.

It is understood that the present invention can be performed on the general population to assess the presence or risk of disease. In another embodiment of the present invention, target patients may be tested to detect a particular type of disease, for example colon cancer. In addition, according to the present invention, subgroups of those patients who already are thought to be at some increased risk, such as e.g., a weak family history, may be tested.

In general, an exemplary kit of the present invention will contain compounds suitable for detecting biomarker(s) associated with differentiation state of a cell. The biomarker can include, but is not limited to, Shh (Sonic hedgehog), Tcf4, Lef1, Twist, EphB2, EphB3, Hes1, Notch1, Hoxa9, Dkk1, Tle6, Tcf3, Bmi1, Kit, Musashi1 (Msi1), Cdx1, Hes5, Oct4, Ki-67, β-catenin, Noggin, BMP4, PTEN (phosphorylated PTEN), Akt (phosphorylated Akt), Villin, Aminopeptidase N (anpep), Sucrase isomaltase (SI), Ephrin-B1 (EfnB1), Cdx2, Crip, Apoa1, Aldh1b1, Calb3, Dgat1, Dgat2, Clu, Hephaestin, Gas1, Ihh (Indian hedgehog), Intrinsic factor B12 receptor, IFABP, or KLF4. As discussed below, a biomarker can be detected using proteomic and microarray techniques. The equipment, instructions and reagents necessary for detecting a cell differentiation-related biomarker can be included a kit of the invention.

As described above, a kit may optionally include one or more probes or primers which can identify a specific imprinted gene or group of genes. Typically, such probes will be nucleic acids or monoclonal antibodies and will be linked to, for example, a fluorescent label. In the case of detecting LOI by relying on the differential rates of transcription of two polymorphic alleles, the kit may comprise means for the amplification of the mRNAs corresponding to the two polymorphic alleles of the gene in question. Examples of such means include suitable DNA primers for the PCR amplification of the mRNAs corresponding to the two polymorphic alleles of the gene in question. Specific examples of such means includes any pair of DNA primers which will anneal to and amplify any gene which is normally imprinted and in which a polymorphism is present. The kit may further include means for identifying the products of the amplification of the mRNAs corresponding to the two polymorphic alleles of the gene in question. Such means include, but is not limited to, a restriction enzyme which specifically cleaves one of the products of the amplification of the mRNAs corresponding to the two polymorphic alleles of the gene in question. Specific examples of such enzymes include, but are not limited to, Apa I in the case of the IGF2 gene. As described below, a kit of the invention may optionally include devices, reagents and/or instructions for testing a sample using proteomic and microarray technology.

Proteomics and Microarrays

Proteomics provides methods for predicting an increased risk of developing a cell proliferation or neoplastic disorder in a subject well before neoplastic tissue is identified in the subject. Proteomics is an evolving technology capable of testing for the presence of minute amounts of a vast array of proteins using small samples of human tissue. Using proteomic tools, increased or decreased levels of certain proteins in a biological sample such as intestinal tissue urine or serum, can be ascertained. In addition, using mathematical algorithms a complex proteome or "fingerprint" can be obtained. As previously noted, such algorithms include "factor analyses" and "principle component analysis (PCA)." The proteome can consist of a group of proteins, some increased in concentration from normal and others decreased, that are indicative of an increased risk of developing a cell proliferation or neoplastic disorder, such as those associated with colon or pancreatic cancer.

Thus, in another embodiment, a method of determining whether a subject is predisposed to developing a cell proliferation or neoplastic disorder using proteomic and/or microarray technology is provided. The method can include obtaining a biological sample from a subject and contacting the sample with an array of immobilized biomolecules that specifically interact with a biomarker indicative of a differentiated or undifferentiated cell. The method may further include obtaining a subject profile by detecting a modification of the biomolecules that is indicative of the ratio of differentiated to undifferentiated cells in the sample and comparing the subject profile with a reference profile. Generally, the reference profile includes one or more values, each value representing the level of biomarker in a reference sample obtained from one or more reference subjects displaying normal imprinting of a target gene. Optionally, the method includes identifying, in the same or different sample, cells displaying abnormal expression of at least one target gene in a normal biological sample from the subject.

A "subject" profile is generally described as a "test" profile. A subject profile can be generated from a sample taken from a subject in order to identify the subject's risk of developing a cell proliferation or neoplastic disorder. Thus, a "subject" profile is generated from a subject being tested for a predisposition to such a disorder. The subject profile can include, for example, the previously discussed ratio obtained from identifying differentiated and undifferentiated cells in a sample. In general, a "reference" profile can be described as a "control" profile. A reference profile can be generated from a sample taken from a particular tissue of a normal individual, or series of individuals, or those having a cell proliferation or neoplastic disorder. The reference profile, or plurality of reference profiles, can be used to establish threshold values for the levels of, for example, specific levels of biomarkers in a particular tissue sample, such as those associated with epithelial cells obtained from crypts of the intestinal lumen. A "reference" profile can include a profile generated from normal subjects or a profile generated from subjects having a cell proliferative disorder. As previously noted, subject profiles and reference profiles can be expressed as an array "signature" or "pattern" of specific identifiable biomarkers. The array signature can be color-coded as in for easy visual or computer-aided identification. The signature can also be described as a number(s) that correspond to values attributed to the biomarkers identified by the array.

The invention provides an array (i.e., "biochip" or "microarray") that includes immobilized biomolecules that facilitate the detection of a particular molecule or molecules in a biological sample. Biomolecules that identify the biomarkers described above (e.g., biomarkers that distinguish differentiated from undifferentiated cells) can be included in a custom array for detecting subjects predisposed to a cell proliferation or neoplastic disorder. For example, a custom array can include biomolecules that identify villin or twist. Arrays comprising biomolecules that specifically identify selected biomarkers can be used to develop a database of information using data provided in the present specification. Additional biomolecules that identify factors related to cellular differentiation which lead to improved cross-validated error rates in multivariate prediction models (e.g., logistic regression, discriminant analysis, or regression tree models) can be included in a custom array of the invention.

The term "array," as used herein, generally refers to a predetermined spatial arrangement of binding islands, biomolecules, or spatial arrangements of binding islands or biomolecules. Arrays according to the present invention that include biomolecules immobilized on a surface may also be referred to as "biomolecule arrays." Arrays according to the present invention that comprise surfaces activated, adapted, prepared, or modified to facilitate the binding of biomolecules to the surface may also be referred to as "binding arrays." Further, the term "array" may be used herein to refer to multiple arrays arranged on a surface, such as would be the case where a surface bore multiple copies of an array. Such surfaces bearing multiple arrays may also be referred to as "multiple arrays" or "repeating arrays." The use of the term "array" herein may encompass biomolecule arrays, binding arrays, multiple arrays, and any combination thereof, the appropriate meaning will be apparent from context. An array can include biomolecules that distinguish differentiated from undifferentiated cells. The biological sample can include fluid or solid samples from any tissue of the body including excretory fluids such as urine.

An array of the invention comprises a substrate. By "substrate" or "solid support" or other grammatical equivalents, herein is meant any material appropriate for the attachment of biomolecules and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, ceramics, and a variety of other polymers. In addition, as is known the art, the substrate may be coated with any number of materials, including polymers, such as dextrans, acrylamides, gelatins or agarose. Such coatings can facilitate the use of the array with a biological sample derived from urine or serum.

A planar array of the invention will generally contain addressable locations (e.g., "pads", "addresses" or "microlocations") of biomolecules in an array format. The size of the array will depend on the composition and end use of the array.

Arrays containing from about 2 different biomolecules to many thousands can be made. Generally, the array will comprise from two to as many as 100,000 or more, depending on the end use of the array. A microarray of the invention will generally comprise at least one biomolecule that identifies or "captures" a biomarker, such as, for example, villin, ephrin-B1, musashi1, or twist, or antagonist thereof, present in a biological sample. In some embodiments, the compositions of the invention may not be in an array format; that is, for some embodiments, compositions comprising a single biomolecule may be made as well. In addition, in some arrays, multiple substrates may be used, either of different or identical compositions. Thus, for example, large planar arrays may comprise a plurality of smaller substrates.

As an alternative to planar arrays, bead based assays in combination with flow cytometry have been developed to perform multiparametric immunoassays. In bead based assay systems the biomolecules can be immobilized on addressable microspheres. Each biomolecule for each individual immunoassay is coupled to a distinct type of microsphere (i.e., "microbead") and the immunoassay reaction takes place on the surface of the microspheres. Dyed microspheres with discrete fluorescence intensities are loaded separately with their appropriate biomolecules. The different bead sets carrying different capture probes can be pooled as necessary to generate custom bead arrays. Bead arrays are then incubated with the sample in a single reaction vessel to perform the immunoassay.

Product formation of the biomarker with their immobilized capture biomolecules can be detected with a fluorescence based reporter system. Biomarkers can either be labeled directly by a fluorogen or detected by a second fluorescently labeled capture biomolecule. The signal intensities derived from captured biomarkers are measured in a flow cytometer. The flow cytometer first identifies each microsphere by its individual color code. Second the amount of captured biomarkers on each individual bead is measured by the second color fluorescence specific for the bound target. This allows multiplexed quantitation of multiple targets from a single sample within the same experiment. Sensitivity, reliability and accuracy are compared to standard microtiter ELISA procedures. With bead based immunoassay systems cytokines can be simultaneously quantified from biological samples. An advantage of bead based systems is the individual coupling of the capture biomolecule to distinct microspheres.

Thus, microbead array technology can be used to sort cell differentiation markers, bound to a specific biomolecule using a plurality of microbeads, each of which can carry about 100,000 identical molecules of a specific anti-tag biomolecule on the surface of a microbead. Once captured, the biomarker can be handled as fluid, referred to herein as a "fluid microarray."

An array of the present invention encompasses any means for detecting a biomarker molecule such as a cell differentiation marker, or antagonist thereof. For example, microarrays can be biochips that provide high-density immobilized arrays of recognition molecules (e.g. antibodies), where biomarker binding is monitored indirectly (e.g. via fluorescence). In addition, an array can be of a format that involves the capture of proteins by biochemical or intermolecular interaction, coupled with direct detection by mass spectrometry (MS).

Arrays and microarrays that can be used with the new methods to detect the biomarkers described herein can be made according to the methods described in U.S. Pat. Nos. 6,329,209; 6,365,418; 6,406,921; 6,475,808; and 6,475,809, and U.S. patent application Ser. No. 10/884,269, which are incorporated herein in their entirety. New arrays, to detect specific selections of sets of biomarkers described herein can also be made using the methods described in these patents.

In many embodiments, immobilized biomolecules, or biomolecules to be immobilized, are proteins. One or more types of proteins may be immobilized on a surface. In certain embodiments, the proteins are immobilized using methods and materials that minimize the denaturing of the proteins, that minimize alterations in the activity of the proteins, or that minimize interactions between the protein and the surface on which they are immobilized.

Surfaces useful according to the present invention may be of any desired shape (form) and size. Non-limiting examples of surfaces include chips, continuous surfaces, curved surfaces, flexible surfaces, films, plates, sheets, tubes, and the like. Surfaces preferably have areas ranging from approximately a square micron to approximately 500 $cm^2$. The area, length, and width of surfaces according to the present invention may be varied according to the requirements of the assay to be performed. Considerations may include, for example, ease of handling, limitations of the material(s) of which the surface is formed, requirements of detection systems, requirements of deposition systems (e.g., arrayers), and the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within wells of 96, 384, 1536, or 3456 microwell plates. In such embodiments, the bottoms of the wells may serve as surfaces for the formation of arrays, or arrays may be formed on other surfaces then placed into wells. In certain embodiments, such as where a surface without wells is used, binding islands may be formed or biomolecules may be immobilized on a surface and a gasket having holes spatially arranged so that they correspond to the islands or biomolecules may be placed on the surface. Such a gasket is preferably liquid tight. A gasket may be placed on a surface at any time during the process of making the array and may be removed if separation of groups or arrays is no longer necessary.

The immobilized biomolecules can bind to molecules present in a biological sample overlying the immobilized biomolecules. Alternatively, the immobilized biomolecules modify or are modified by molecules present in a biological sample overlying the immobilized biomolecules. For example, a cell differentiation marker present in a biological sample can contact an immobilized biomolecule and bind to it, thereby facilitating detection of the marker. Alternatively, the cell differentiation marker, or antagonist thereof, can contact a biomolecule immobilized on a solid surface in a transient fashion and initiate a reaction that results in the detection of the marker absent the stable binding of the marker to the biomolecule.

Modifications or binding of biomolecules in solution or immobilized on an array may be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces may be measured; techniques using radioisotopes, including conventional radioisotope binding and scintillation proximity assays so (SPA); mass spectroscopy, such as matrix-assisted laser desorption/ionization mass spectroscopy (MALDI) and MALDI-time of flight (TOF) mass spectropscopy; ellipsometry, which is an optical method of measuring thickness of protein films; quartz crystal microbalance (QCM), a very sensitive method for measuring mass of materials adsorbing to surfaces; scanning probe microscopies, such as AFM and SEM; and techniques such as electrochemical, impedance, acoustic, microwave, and IR/Raman detection. See, e.g., Mere L, et al., "Miniaturized FRET assays and microfluidics: key components for ultra-high-throughput screening," Drug Discovery Today 4(8):363-369 (1999), and references cited therein; Lakowicz J R, Principles of Fluorescence Spectroscopy, 2nd Edition, Plenum Press (1999).

Arrays of the invention suitable for identifying an increased risk of developing a cell proliferation or neoplastic disorder may be included in kits. Such kits may also include, as non-limiting examples, reagents useful for preparing biomolecules for immobilization onto binding islands or areas of an array, reagents useful for detecting modifications to immobilized biomolecules, or reagents useful for detecting binding of biomolecules from solutions of interest to immobilized biomolecules, and instructions for use. Thus, in another embodiment, a diagnostic kit for detecting a cell proliferation or neoplastic disorder, or a predisposition to a cell proliferation or neoplastic disorder, is provided. Such kits can include a means for identifying a subject comprising cells displaying abnormal imprinting of at least one target gene and an array for detecting a biomarker indicative of a differentiated or undifferentiated cells, the array comprising a substrate having a plurality of addresses, each address having disposed thereon an immobilized biomolecule. Each biomolecule can individually detect a biomarker indicative of a differentiated or undifferentiated cells. As will be discussed below, in addition to identifying subjects predisposed to developing a neoplastic disorder, methods provided herein can be used to follow the progress of a subject undergoing treatment for such a disorder.

Theranostics

The invention provides compositions and methods for the identification of a predisposition to a cell proliferation or neoplastic disorder such that a theranostic approach can be taken to test such individuals to determine the effectiveness of a particular therapeutic intervention (pharmaceutical or non-pharmaceutical) and to alter the intervention to 1) reduce the risk of developing adverse outcomes and 2) enhance the effectiveness of the intervention. Thus, in addition to diagnosing or confirming the presence of or risk for a gestational disorder, the methods and compositions of the invention also provide a means of optimizing the treatment of a subject having such a disorder. The invention provides a theranostic approach to treating a cell proliferation or neoplastic disorder by integrating diagnostics and therapeutics to improve the real-time treatment of a subject having, for example, LOI of the IGF2 gene. Practically, this means creating tests that can identify which patients are most suited to a particular therapy, and providing feedback on how well a drug is working to optimize treatment regimens. In the area of diseases associated with cell proliferation or neoplastic disorders, theranostics can flexibly monitor changes in important parameters (e.g., an increase or decrease in the ratio of differentiated vs. undifferentiated cells in a tissue sample) over time. For example, theranostic multiparameter immunoassays specific for a series of diagnostically relevant molecules such as those that distinguish differentiated from undifferentiated cells can be used to follow the progress of a subject undergoing treatment for the prevention of colon cancer.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

Statistical Analyses

The data presented herein provides a database of information related to diagnosing cell proliferation or neoplastic disorders. Prediction rules can be selected based on cross-validation, and further validating the chosen rule on a separate cohort. A variety of approaches can be used to generate data predictive of a cell proliferation or neoplastic disorder based on cell differentiation marker levels provided herein, including discriminant analysis, logistic regression, and regression trees.

Discriminant analysis attempts to find a plane in the multivariate space of the marker data such that, to the extent possible, cases appear on one side of this plane, and controls on the other. The coefficients which determine this plane constitute a classification rule: a linear function of the marker values which is compared with a threshold. In Bayesian classification, information on the probability of a subject being a case (i.e., a subject having, or predisposed to having, a cell proliferation or neoplastic disorder) that is known before the data are obtained can be employed. For example the prior probability of being a case can be set to about 0.5; for a screening test applied to a general population the corresponding probability will be approximately 0.05. A subject is classified as having, or at risk of having, a complication (i.e., a cell proliferation or neoplastic disorder) if the corresponding posterior probability (i.e., the prior probability updated using the data) exceeds 0.5.

Additional patient information (e.g., LOI and/or family history) can be combined with the cell differentiation markers provided herein. These data can be combined in a database that analyzes the information to identify trends that complement the present biomarker data. Results can be stored in an electronic format.

Additional analyses can be performed to identify subjects at risk for cell proliferation or neoplastic disorders such as colon cancer or pancreatic cancer. Such analyses include bivariate analysis of each of the primary exposures, multivariate models including variables with a strong relationship (biologic and statistical) with outcomes, methods to account for multiple critical exposures including variable reduction using factor analysis, and prediction models.

For bivariate analysis, the mean level of each primary exposure between cases and controls using a 2-sample t-test or Wilcoxon Rank Sum test, as appropriate, can be conducted. If the association appears linear, trend can be analyzed using the Mantel Haenszel test. Data can be assembled into less fine categories (e.g., tertiles) using the distribution of the controls, and examine these as indicator variables in multivariable analysis.

For multivariate analyses, data can be correlated between two control groups, one matched and another not matched. In both matched and unmatched analyses, the independent effects of all primary exposures of interest can be examined using logistic regression (with conditional models in matched analyses) models. The models can include a minimum number of covariates to test the main effect of specific predictors.

Databases and Computerized Methods of Analyzing Data

A database generated from the methods provided herein and the analyses described above can be included in, or associated with, a computer system for determining whether a subject has, or is predisposed to having, a cell proliferation or neoplastic disorder. The database can include a plurality of digitally-encoded "reference" (or "control") profiles. Each reference profile of the plurality can have a plurality of values, each value representing a level of a biomarker in a sample. Alternatively, a reference profile can be derived from an individual that is normal. Both types of profiles can be included in the database for consecutive or simultaneous comparison to a subject profile. The computer system can include a server containing a computer-executable code for receiving a profile of a subject and identifying from the database a matching reference profile that is diagnostically relevant to the subject profile. The identified profile can be supplied to a caregiver for diagnosis or further analysis.

Thus, the various techniques, methods, and aspects of the invention described above can be implemented in part or in whole using computer-based systems and methods. Additionally, computer-based systems and methods can be used to augment or enhance the functionality described above, increase the speed at which the functions can be performed, and provide additional features and aspects as a part of or in addition to those of the invention described elsewhere in this document. Various computer-based systems, methods and implementations in accordance with the above-described technology are presented below.

A processor-based system can include a main memory, preferably random access memory (RAM), and can also include a secondary memory. The secondary memory can include, for example, a hard disk drive and/or a removable storage drive, representing a floppy disk drive, a magnetic tape drive, an optical disk drive, etc. The removable storage drive reads from and/or writes to a removable storage medium. Removable storage medium refers to a floppy disk, magnetic tape, optical disk, and the like, which is read by and written to by a removable storage drive. As will be appreciated, the removable storage medium can comprise computer software and/or data.

In alternative embodiments, the secondary memory may include other similar means for allowing computer programs or other instructions to be loaded into a computer system. Such means can include, for example, a removable storage unit and an interface. Examples of such can include a program cartridge and cartridge interface (such as the found in video game devices), a removable memory chip (such as an EPROM or PROM) and associated socket, and other removable storage units and interfaces, which allow software and data to be transferred from the removable storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, and the like. Software and data transferred via a communications interface are in the form of signals, which can be electronic, electromagnetic, optical or other signals capable of being received by a communications interface. These signals are provided to communications interface via a channel capable of carrying signals and can be implemented using a wireless medium, wire or cable, fiber optics or other communications medium. Some examples of a channel can include a phone line, a cellular phone link, an RF link, a network interface, and other communications channels.

In this document, the terms "computer program medium" and "computer usable medium" are used to refer generally to media such as a removable storage device, a disk capable of installation in a disk drive, and signals on a channel. These computer program products are means for providing software or program instructions to a computer system.

Computer programs (also called computer control logic) are stored in main memory and/or secondary memory. Computer programs can also be received via a communications interface. Such computer programs, when executed, enable the computer system to perform the features of the invention as discussed herein. In particular, the computer programs, when executed, enable the processor to perform the features of the invention. Accordingly, such computer programs represent controllers of the computer system.

In an embodiment where the elements are implemented using software, the software may be stored in, or transmitted via, a computer program product and loaded into a computer system using a removable storage drive, hard drive or communications interface. The control logic (software), when executed by the processor, causes the processor to perform the functions of the invention as described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to person skilled in the relevant art(s). In yet another embodiment, elements are implanted using a combination of both hardware and software.

In another embodiment, the computer-based methods can be accessed or implemented over the World Wide Web by providing access via a Web Page to the methods of the invention. Accordingly, the Web Page is identified by a Universal Resource Locator (URL). The URL denotes both the server machine and the particular file or page on that machine. In this embodiment, it is envisioned that a consumer or client computer system interacts with a browser to select a particular URL, which in turn causes the browser to send a request for that URL or page to the server identified in the URL. Typically the server responds to the request by retrieving the requested page and transmitting the data for that page back to the requesting client computer system (the client/server interaction is typically performed in accordance with the hypertext transport protocol ("HTTP")). The selected page is then displayed to the user on the client's display screen. The client may then cause the server containing a computer program of the invention to launch an application to, for example, perform an analysis according to the invention.

The invention is further described in the following examples, which serve to illustrate but not to limit the scope of the invention described in the claims.

EXAMPLES

Figure 3:
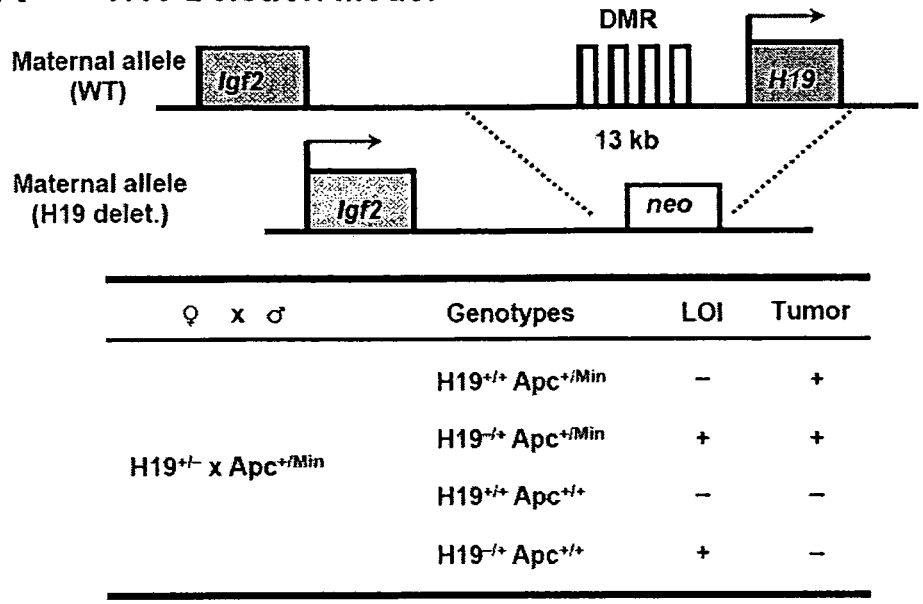
FIG. 3, panels A-C, depict mouse models of H19 deletion and DMR mutation.
Figure 3:
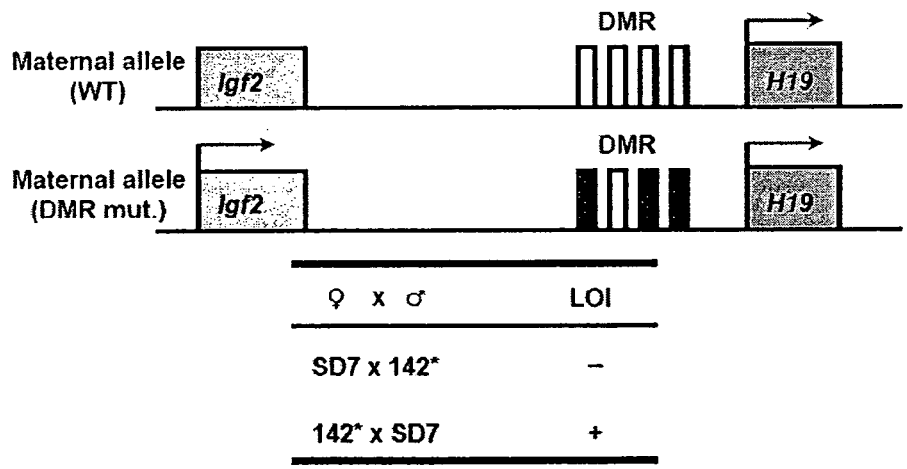
Figure 4:
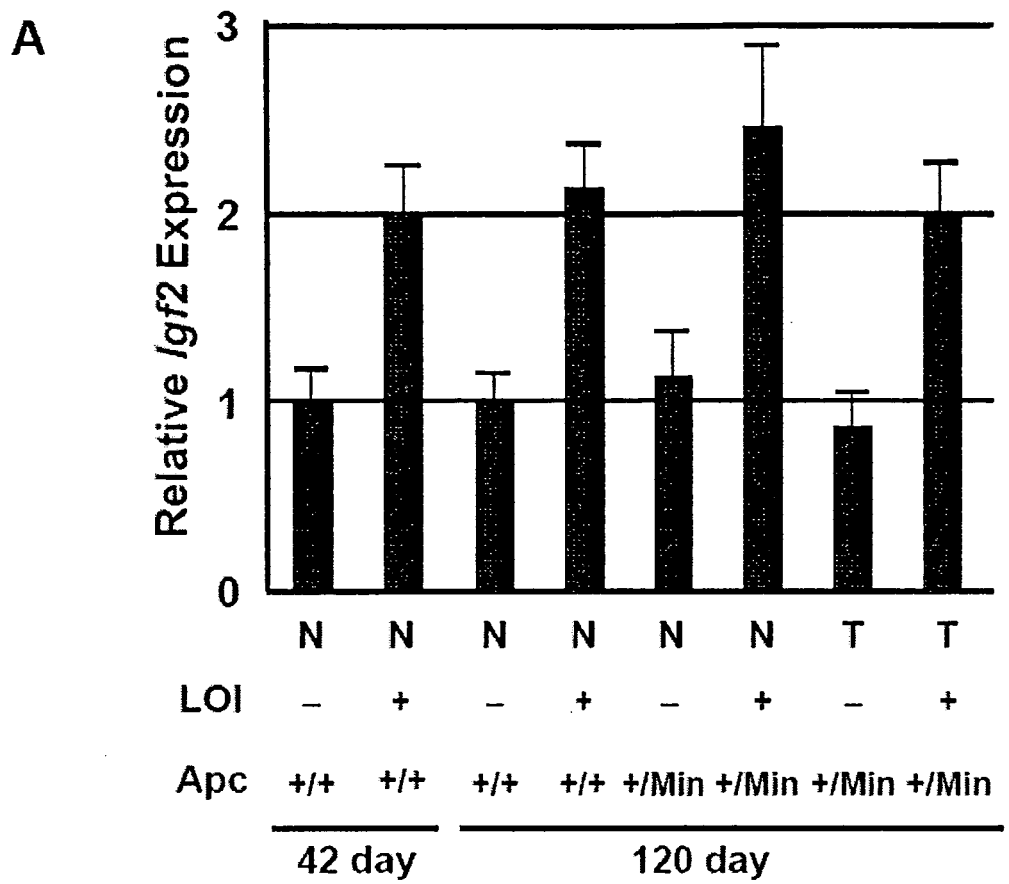
FIG. 4, panels A and B, depict Igf2 mRNA and protein levels.
Figure 4:
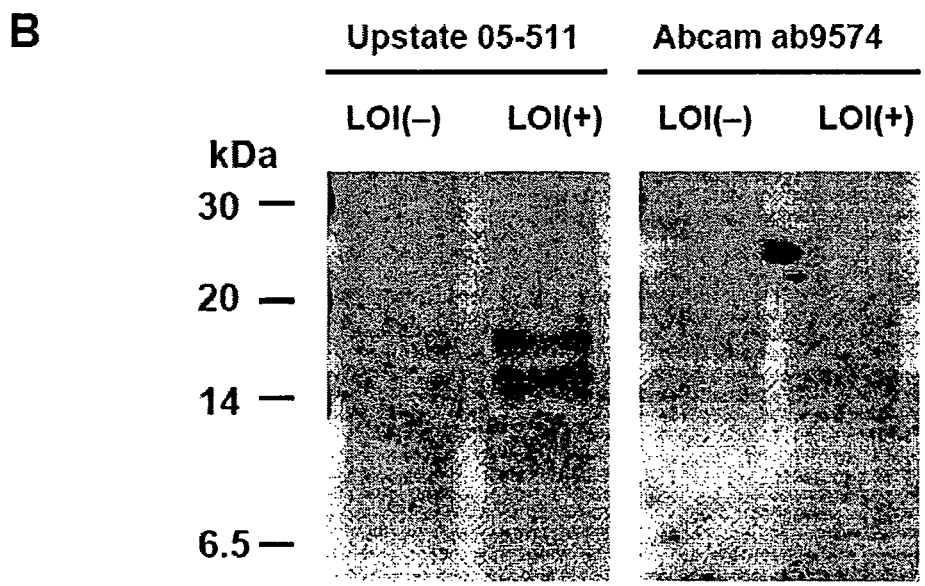
Figure 5:
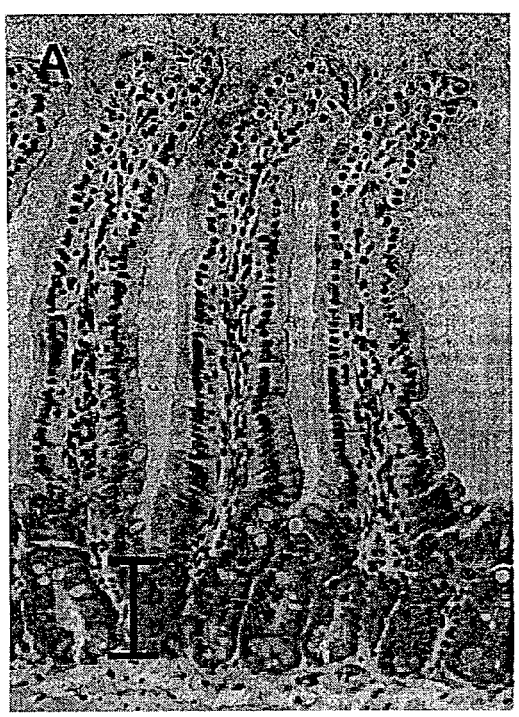
FIG. 5, panels A and B, depict histomorphology of small intestinal mucosa in LOI(−) mice (panel A) versus LOI(+) mice (panel B).
Figure 5:
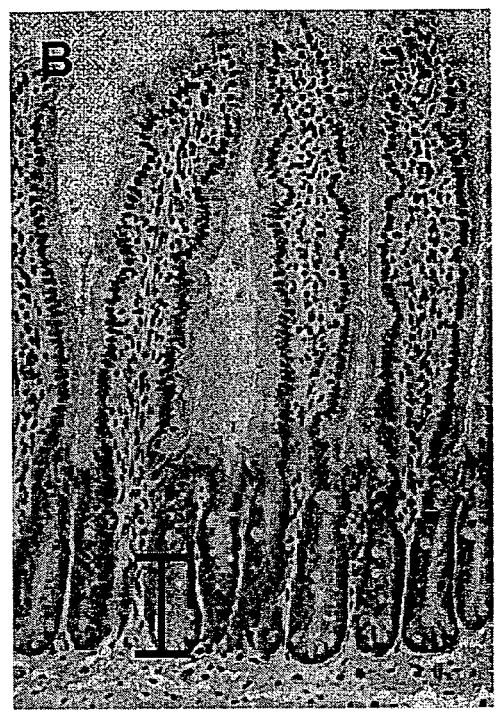

A mouse model was created to investigate the mechanism by which LOI of IGF2 contributes to intestinal tumorigenesis. Previous analyses of mouse models by other groups have shown that Igf2 is activated more than 25-fold in pancreatic tumors induced by the SV40 large T antigen (Christofori, et al., Nat. Genet. 10, 196 (1995)) and that forced overexpression of Igf2 causes intestinal tumor formation and hyperproliferation of crypt epithelium (Hassan and Howell, Cancer Res. 60, 1070 (2000); Bennett, et al., Development 130, 1079 (2003)). The model provided herein was designed to mimic the human situation, where LOI causes only a modest increase in IGF2 expression. Imprinting of Igf2 is regulated by a differentially methylated region (DMR) upstream of the nearby untranslated H19 gene. Deletion of the DMR leads to biallelic expression (LOI) of Igf2 in the offspring when the deletion is maternally inherited (FIG. 3). To model intestinal neoplasia, we used Min mice with an Apc mutation (Su et al., Science 256, 668 (1992)). We crossed female H19+/−with male Apc+/Min, comparing littermates harboring Apc mutations with or without a maternally inherited H19 deletion, and thus with or without LOI. In comparison with H19+/+ [hereafter referred to as LOI(−) mice], the H19−/+ mutant mice [hereafter referred to as LOI(+) mice] showed an approximate doubling in Igf2 mRNA levels that did not vary with age or Min status (FIG. 4). This is consistent with the 2 to 3-fold increase in Igf2 mRNA levels in normal human colonic mucosa or Wilms tumors that are LOI(+) (Ravenel et al., J. Natl. Cancer Inst. 93, 1698 (2001)). The level of Igf2 protein was also doubled in the intestine of LOI(+) mice (FIG. 4). The LOI(+) mice developed about twice as many adenomas in both small intestine and colon as did the LOI(−) mice, and this difference was statistically significant (Table 1). Mice with LOI also had longer intestinal crypts, the site of epithelial stem cell renewal (Sell and Pierce, Lab. Invest. 70, 6 (1994)) (FIG. 5). This increase in length was specific to the crypts, progressed over time [1.2-fold increase (P<0.01) in mice at 42 days of age and 1.5-fold increase (P<0.0001) in mice at 120 days], and was independent of Apc status. The increase in crypt length was not due to differences in cell proliferation, as there was no statistically significant difference in proliferating cell nuclear antigen labeling index between LOI(+) and LOI(−) Min mice (3.8±0.9 vs. 3.1±1.5, respectively), nor was there a difference in the distribution (Lipkin and Deschner, Cancer Res 36, 2665 (1976)) of proliferative cells within the crypt (0.39±0.04 vs. 0.38±0.03, respectively, P=N.S.). The LOI(+) and LOI(−) mice showed no difference in crypt apoptotic rates, as assessed histomorphologically and by in situ TUNEL assay; both genotypes had an average of 1 apoptotic cell per 20 crypts. There was also no difference in the rate of branching of intestinal crypts; both LOI(+) and LOI(−) mice had 1-2 total branched crypts below the intestinal surface.

Increased crypt length of the small intestine correlates with a shift in the ratio of undifferentiated to differentiated epithelial cells in the mucosa. Four antigens were immunostained to distinguish undifferentiated versus differentiated epithelial cell development: villin, a structural component of the brush border cytoskeleton in gastrointestinal tract epithelia (West et al., Gastroenterol. 94, 343 (1988)); ephrin-B1, the ligand of the EphB2/EphB3 receptors that play a role in allocating epithelial cells within the crypt-villus axis in intestinal epithelium (Batlle et al., Cell 111, 251 (2002)); musashi1, an RNA-binding protein selectively expressed in neural and intestinal progenitor cells and key to maintaining the stem cell state (Kaneko et al., Dev. Neurosci. 22, 139 (2000); Potten et al., Differentiation 71, 28 (2003)); and twist, a transcriptional factor of the basic helix-loop-helix family originally identified as a mesodermal progenitor cell marker (Borkowski, et al., Development 121, 4183 (1995)) that is also involved in loss of differentiation of epithelial cells (Howe, et al., Cancer Res. 63, 1906 (2003); Thiery and Morgan, Nat. Med. 10, 777 (2004)).

FIG. 1 depicts immunohistochemical analysis of villin and musashi1 in 120 day old LOI(−) and LOI(+) mice. Panel A shows, in LOI(−) mice, villin protein expression is noted in a cytoplasmic distribution throughout differentiated enterocytes lining intestinal villi and within the crypt-villus interface. Panel B shows, in LOI(+) mice, villin expression is markedly decreased. Panel C shows, in LOI(−) mice, musashi1 expression is detected within the cytoplasm and nuclei in rare cells within intestinal crypts (arrow), the location of intestinal stem cells and the undifferentiated epithelial cell compartment. Panel D shows that, in contrast to panel C, musashi1 cytoplasmic and nuclear labeling is detected throughout the intestinal crypts of LOI(+) mice. Panel E shows that, in LOI(−) mice, rare musashi1-positive cells are detected within the overlying intestinal villi representing the differentiated epithelial compartment. Panel F shows that, in LOI(+) mice, intense cytoplasmic and nuclear expression of musashi1 is detected within enterocytes lining intestinal villi. Scale bars correspond to 110 μm.

Figure 6:
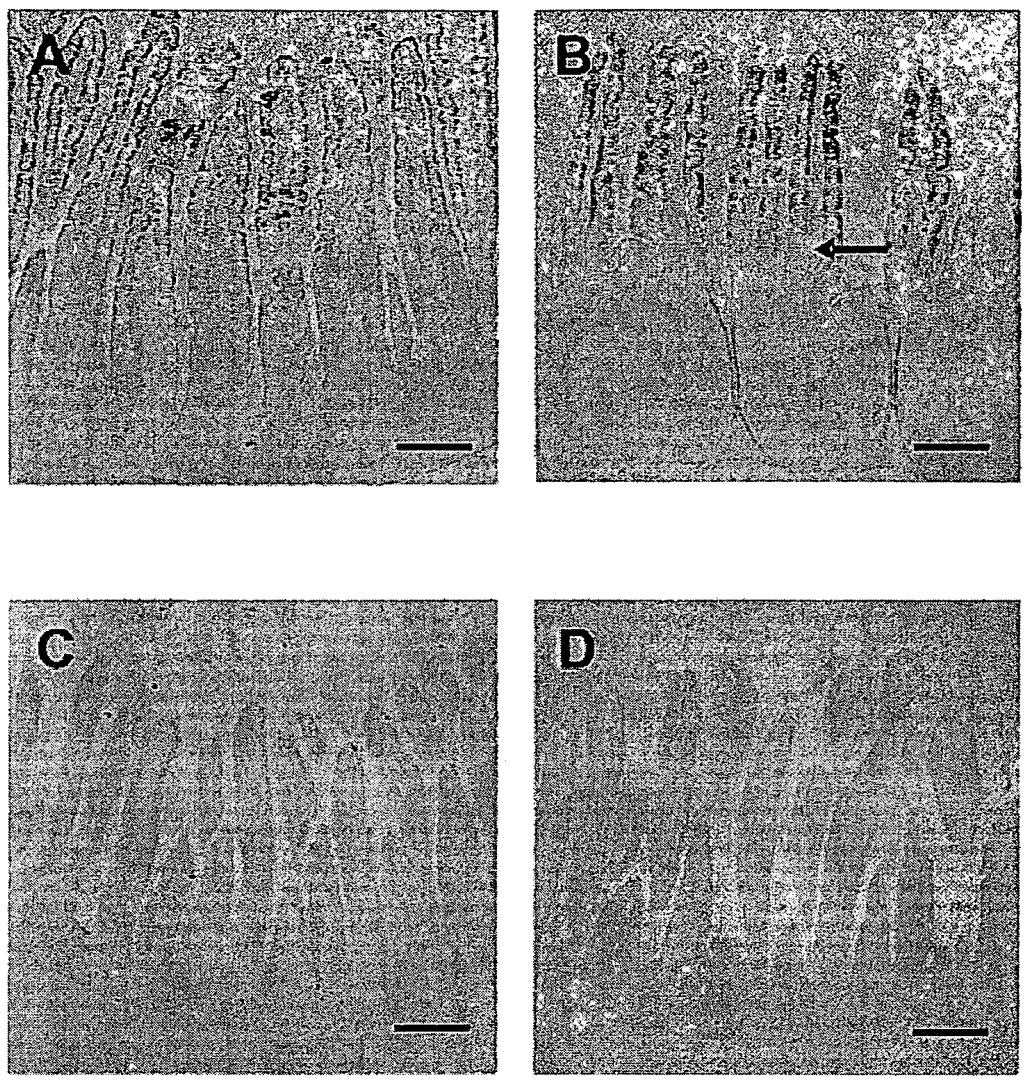
FIG. 6, panels A-D, depict immunohistochemistry for villin and ephrin-B1 in 42 day mice.

Consistent with their biologic roles in differentiated enterocytes, immunostaining for both villin and ephrin-B1 were detected within the cytoplasm of enterocytes lining the villi of the small intestine and within the villus-crypt interface in LOI(−) mice (FIG. 1, panel A) (FIG. 6). The LOI(+) mice, in contrast, showed lower levels of villin and ephrin-B1 and a contraction of the differentiated epithelial cell compartment (FIG. 1, panel B) (FIG. 6).

Figure 7:
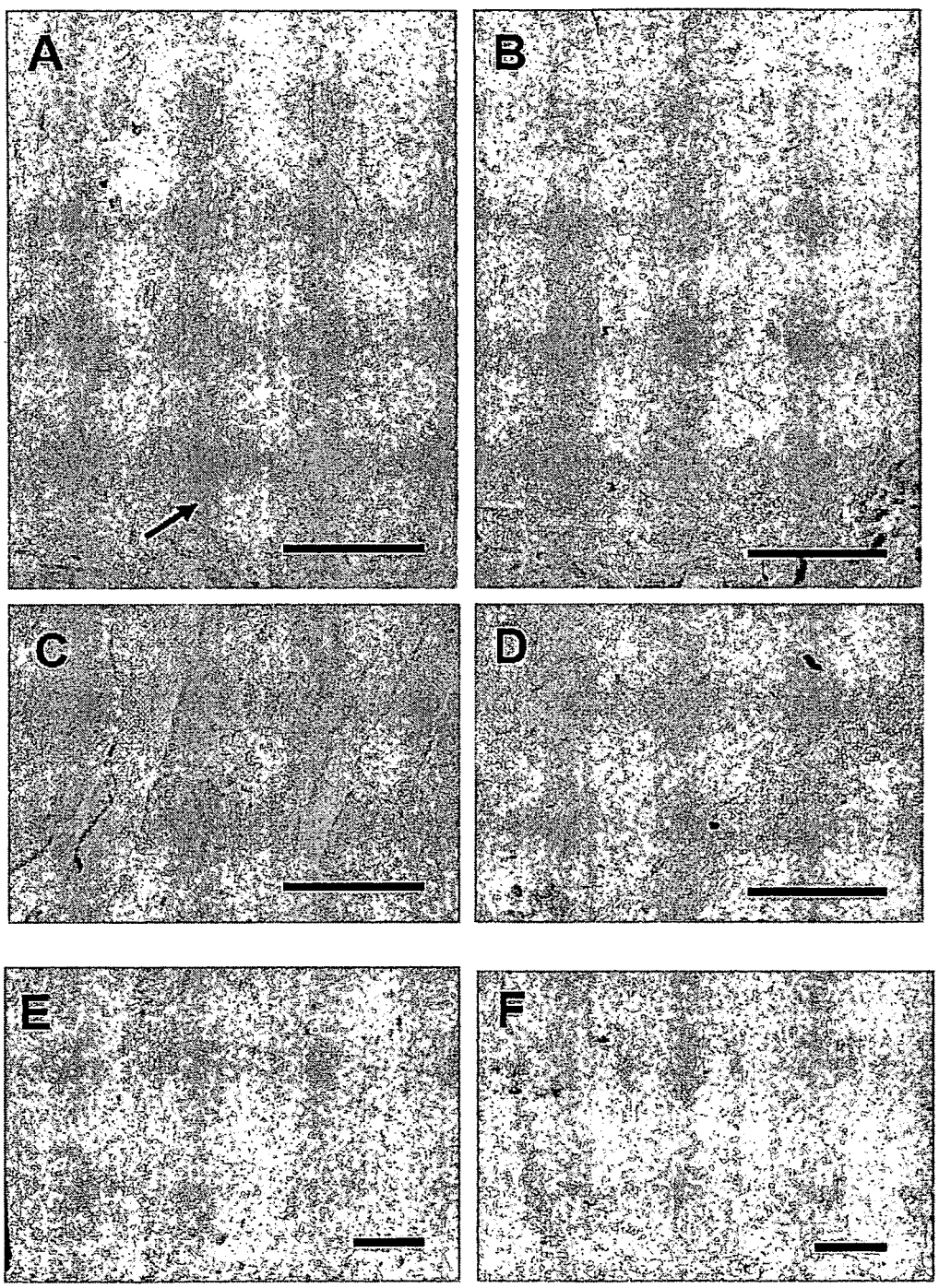
FIG. 7, panels A-F, depict immunohistochemistry for musashi1 and twist in 42 day mice.

Expression of the progenitor cell marker musashi1 was observed in scattered cells within the lower half of intestinal crypts in LOI(−) mice (FIG. 1, panel C), whereas numerous musashi1-positive cells were identified within the intestinal crypts of LOI(+) mice (FIG. 1, panel D). The LOI(+) mice also showed intense staining within enterocytes lining the intestinal villi compared with LOI(−) mice (FIG. 1, panels E-F). A semi-quantitative analysis confirmed increased musashi1 staining in the LOI(+) mice, independent of Apc status (Table 2). Immunostaining for twist also revealed a marked increase in the number and intensity of positively-staining cells in the crypts of LOI(+) mice (FIG. 7). These changes were progressive over time (see e.g., FIGS. 1, 6 and 7).

Because this shift affects normal mucosa, one prediction of this de-differentiation model is that the increased number of adenomas is due to an increase in tumor initiation rather than an increase in tumor progression. Supporting this idea, there was no difference in the ratio of microadenomas [<5 crypts each, (Torrance et al., Nat. Med. 6, 1024 (2000))] to macroadenomas (≥5 crypts each) between LOI(+) Min mice (36 micro/27 macro) and LOI(−) Min mice (16 micro/14 macro) at 120 days. An independent mouse model of LOI, in which point mutations had been introduced in three of the four CCCTC-binding factor (CTCF) target sites within the H19 DMR (Pant et al., Genes Dev. 17, 586 (2003)) (FIGS. 3 and 8), was also examined by immunostaining. Another advantage of this model is that, unlike the deletion model, H19 expression is intact in the DMR mutation model (FIG. 9). Loss of H19 might have independent effects given its known role on mRNA translation in trans. Nevertheless, a shift in the ratio of differentiated to undifferentiated cells was also seen in the normal epithelium of these LOI(+) mice. For example, FIG. 2, panels A-H, depict a shift to less differentiated colon epithelium in a mouse H19 DMR mutation model and in colonoscopy clinic patients with LOI. Musashi1 immunostaining in LOI(−) mice shows rare crypt epithelial cells with cytoplasmic labeling (panel A), compared with LOI(+) mice (panel B), which show aberrant musashi1 staining in both a cytoplasmic and nuclear pattern throughout the colonic epithelium. Panel C shows that villin immunostaining in LOI(−) mice shows cytoplasmic labeling including the brush border. In contrast, in LOI(+) mice (panel D), villin staining of the brush border on the surface epithelial cells is absent. Panel E shows that in 12 colonoscopy patients without LOI, rare musashi1-positive cells are detected in crypt epithelial cells (arrow). Low power view is available in FIG. 10. In contrast, panel F shows that in colonoscopy patients with LOI, musashi1 labeling is present throughout colonic crypts with extension to the surface epithelium (see also FIG. 10). In colonoscopy patients without LOI, only weak labeling for twist is detected (see panel G). In colonoscopy patients with LOI, patchy but strong twist labeling is present in the crypt and surface epithelium (see panel H). Scale bars correspond to 10 µm.

FIG. 3, panels A-C, depict mouse models of H19 deletion and DMR mutation. Panel A is a diagram of the H19 deletion model. Thirteen kb including the H19 gene and its DMR in the upstream region were replaced with neo. When this deletion is inherited from the mother, H19 expression is lost and the normally silent Igf2 allele is activated as shown. Experimental crosses were performed between female H19+/− and male Apc+/Min mice to obtain the four genotypes shown. Panel B is a diagram of the H19 DMR mutation model. Three of the four CTCF binding cites at H19 DMR were mutated (closed boxes). When this mutation is inherited from the mother, the normally silent Igf2 allele is activated with H19 expression maintained (see also FIG. 8). DMR-mutant (142*) female or male mice were crossed with wild type SD7 to obtain mice with LOI and normal imprinting of Igf2, respectively. Panel C is a table of experiments performed with each model.

FIG. 4, panels A and B, depict Igf2 mRNA and protein levels. Panel A shows relative Igf2 mRNA level. Igf2 mRNA levels were analyzed by real-time RT-PCR, normalized to that of β-actin, and are displayed relative to the small intestine of wild type LOI(−) mice at 42 days. Igf2 mRNA was 2.0-fold greater in the non-tumor region of LOI(+) mouse intestine than in LOI(−) mouse intestine at 42 days (P=0.002), and 2.1-fold greater at 120 days (P=0.04). For LOI(+) Min mice at 120 days, Igf2 mRNA showed a 2.2-fold increase in the non-tumor region (P=0.03) and a 2.3-fold increase in the tumor region (P=0.003), compared with LOI(−) Min mice. Within a given genotype, the expression of Igf2 did not increase from normal to tumor, consistent with an early role for LOI in tumorigenesis. N, non-tumor region. T, tumor region. P values were calculated by T-test for each comparison. Panel B shows western blot analysis of Igf2 protein. Signals were detected at 15 kDa, 17 kDa and weakly at 18 kDa using two separate antibodies (shown), and the intensities were increased 1.7-2.1 fold (Upstate) and 1.5-2.1 fold (Abcam) in the small intestine of LOI(+) mice, normalized to total protein. These higher molecular weight forms are well described in mammals and are more efficient activators of the Igf1 receptor (the signaling target of Igf2) than is the fully processed form of Igf2.

FIG. 5, panels A and B, depict histomorphology of small intestinal mucosa in LOI(−) mice (panel A) versus LOI(+) mice (panel B). Detailed histopathological exam of the small intestine, colon, and extraintestinal tissues were performed in both 42 day and 120 day (shown) mice. Although no architectural differences are seen in association with LOI status, the crypt length of the small intestine of LOI(+) mice showed a statistically significant increase compared to their wild-type littermates: 1.2-fold increase (15.3±1.9 µm vs. 13.1±1.8 µm, P<0.01) at 42 days; and 1.5-fold increase (19.6±2.0 µm vs. 13.0±2.0 µm, P<0.0001) at 120 days.

FIG. 6, panels A-D, depict immunohistochemistry for villin and ephrin-B1 in 42 day mice. Panel A shows that, in LOI(−) mice, villin is found in a cytoplasmic distribution throughout differentiated enterocytes lining intestinal villi, with expression extending to the transition zone and superficial crypts. Panel B shows that, in LOI(+) mice, villin is largely restricted to the enterocytes lining intestinal villi with no expression noted within the transition zone or superficial crypts (indicated by arrow), consistent with a contraction of the differentiated cell compartment. As shown in panel C, ephrin-B1 protein expression shows a similar pattern as described for villin, seen as cytoplasmic labeling of differentiated enterocytes lining intestinal villi in LOI(−) mice. In contrast, panel D shows that immunostaining for ephrin-B1 is markedly decreased in the intestinal villi of LOI(+) mice.

FIG. 7, panels A-F, depict immunohistochemistry for musashi1 and twist in 42 day mice. Panel A shows that, in LOI(−) mice, musashi1 expression can be detected within the cytoplasm and nuclei in rare cells within intestinal crypts (representatively indicated by arrow). Panel B shows that, in LOI(+) mice, musashi1 cytoplasmic and nuclear labeling can be detected throughout the intestinal crypts. Panel C shows that, in LOI(−) mice, no musashi1 expression is detected within the overlying intestinal villi. Panel D shows that, in LOI(+) mice, ectopic cytoplasmic and nuclear expression is seen in enterocytes lining intestinal villi. Panel E shows weak cytoplasmic twist expression can be detected in rare cells within intestinal crypts in LOI(−) mice. Panel F shows that twist is greatly increased within intestinal crypts of LOI(+) mice.

Figure 8:
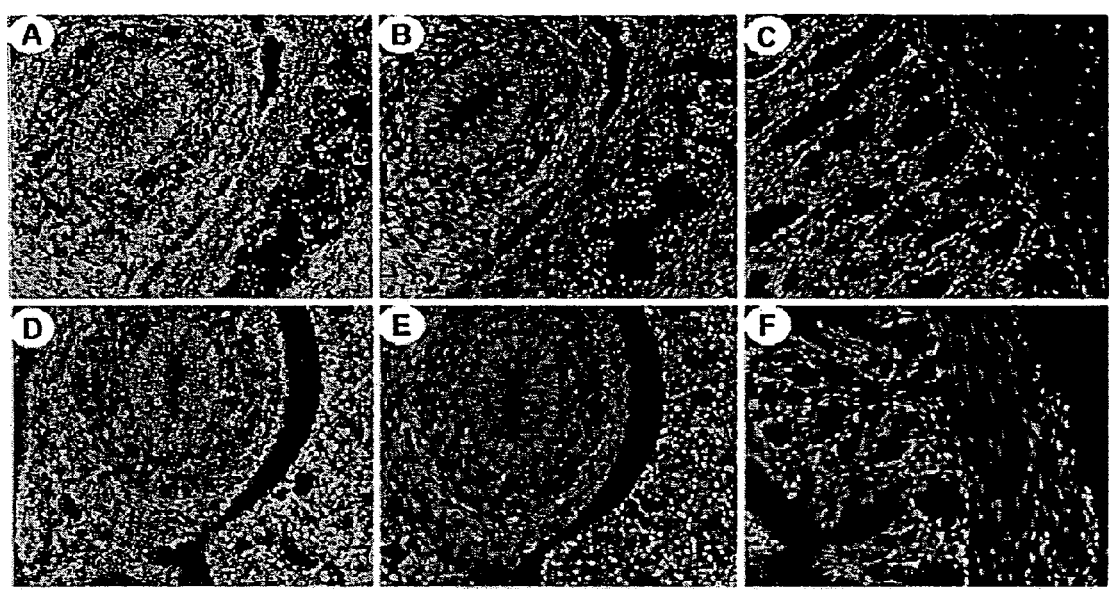
FIG. 8, panels A-F, depict in situ hybridization analysis of Igf2 mRNA levels in mouse gut with mutation in the H19 DMR (142* mouse).
Figure 9:
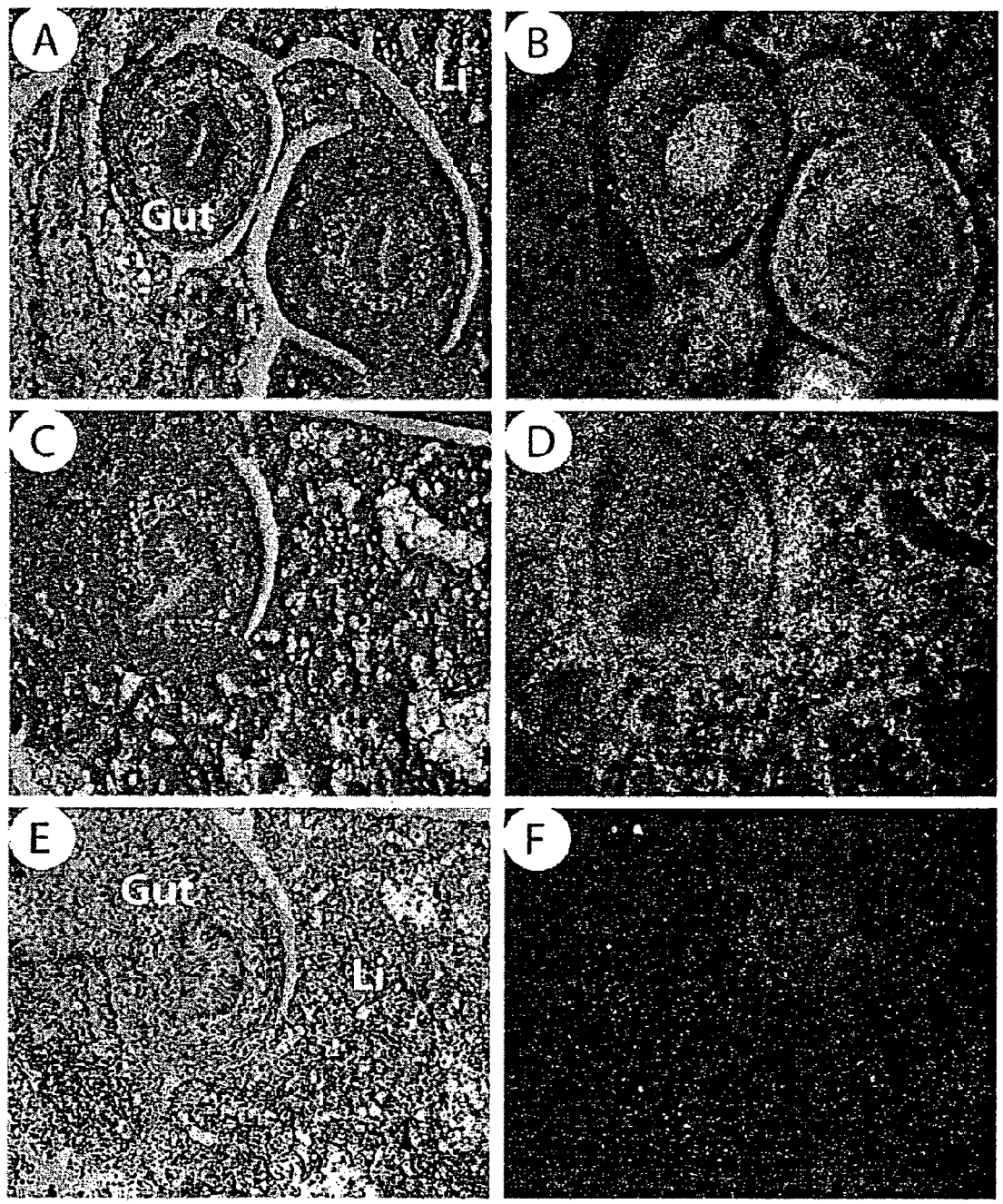
FIG. 9, panels A-F, depict in situ hybridization analysis of H19 mRNA levels in E16.5 mouse embryos with mutation in the H19 DMR.

FIG. 8, panels A-F, depict in situ hybridization analysis of Igf2 mRNA levels in mouse gut with mutation in the H19 DMR (142* mouse). The composite bright- and darkfield images represent: Panel A shows fetal (E16.5) gut in a 142*× SD7 cross, antisense Igf2 riboprobe. Panel B shows fetal gut, 142*×SD7 cross, sense probe. Panel C shows adult (153 day) gut, 142*×SD7 cross, antisense probe. Panel D shows fetal gut, SD7×142* cross, antisense probe. Panel E shows fetal gut, SD7×142* cross, sense probe. Panel F shows adult gut, SD7×142* cross, antisense probe.

FIG. 9, panel A-F, depict in situ hybridization analysis of H19 mRNA levels in E16.5 mouse embryos with mutation in the H19 DMR. Panel A shows a brightfield view over the gut in a 142*×SD7 fetus using antisense Igf2 riboprobe. Panel B shows a darkfield view, 142*×SD7 fetus, antisense probe. Panel C shows a brightfield view, SD7×142* fetus, antisense probe. Panel D shows a darkfield view, SD7×142* fetus, antisense probe. Panel E shows a brightfield view, SD7×142*, sense probe. Panel F shows a darkfield view, SD7×142* fetus, sense probe.

Figure 10:
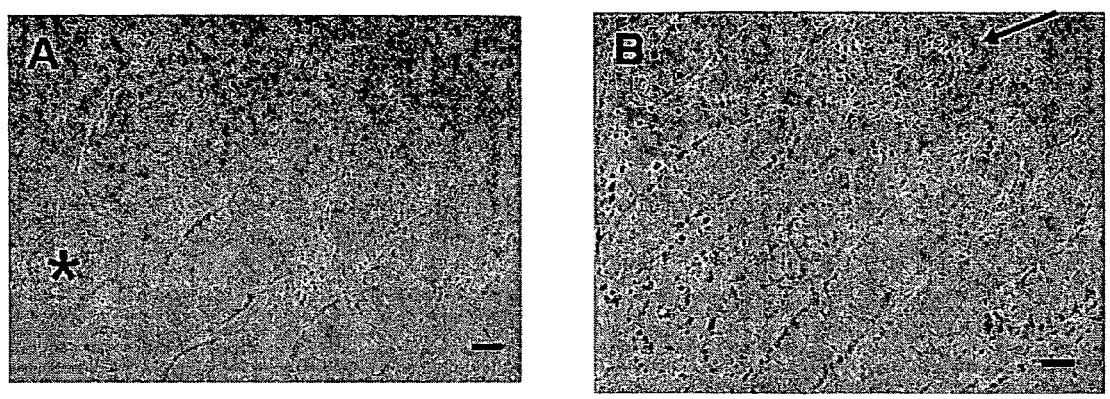
FIG. 10, panels A and B, depict musashi1 immunostaining of normal colon of a colonoscopy patient without LOI and a patient with LOI.

FIG. 10 depicts musashi1 immunostaining of normal colon of a colonoscopy patient without LOI and a patient with LOI. Panel A shows that musashi1 positive cells were rarely observed in colonic crypts of patients without LOI, and there was no surface staining. A higher power view of the crypt indicated by an asterisk is available in FIG. 2, panel E. In contrast, Panel B of FIG. 10 shows that aberrant musashi1 protein expression can be detected in patients with LOI throughout colonic crypts with extension to surface epithelium (surface indicated by arrow). A higher power view of the crypt is available in FIG. 2, panel F.

A comparison was made of normal mucosa of patients requiring biopsy during colonoscopic screening, whose LOI status was previously determined. No morphological differences were noted by conventional microscopy. However, 10 of 11 patients with LOI in the colon showed increased musashi1 staining extending to the upper half of colonic crypts and/or surface epithelium, compared with 5 of 15 patients without LOI (P=0.004, Fisher exact test) (FIG. 2, panels E through F) (FIG. 10). Altered colon epithelial maturation was also found in all 4 patients with LOI restricted to the colon (P=0.03), and in 6 of 7 patients with LOI in both peripheral blood lymphocytes and colon (P=0.03), compared with patients without LOI.

Figure 2:
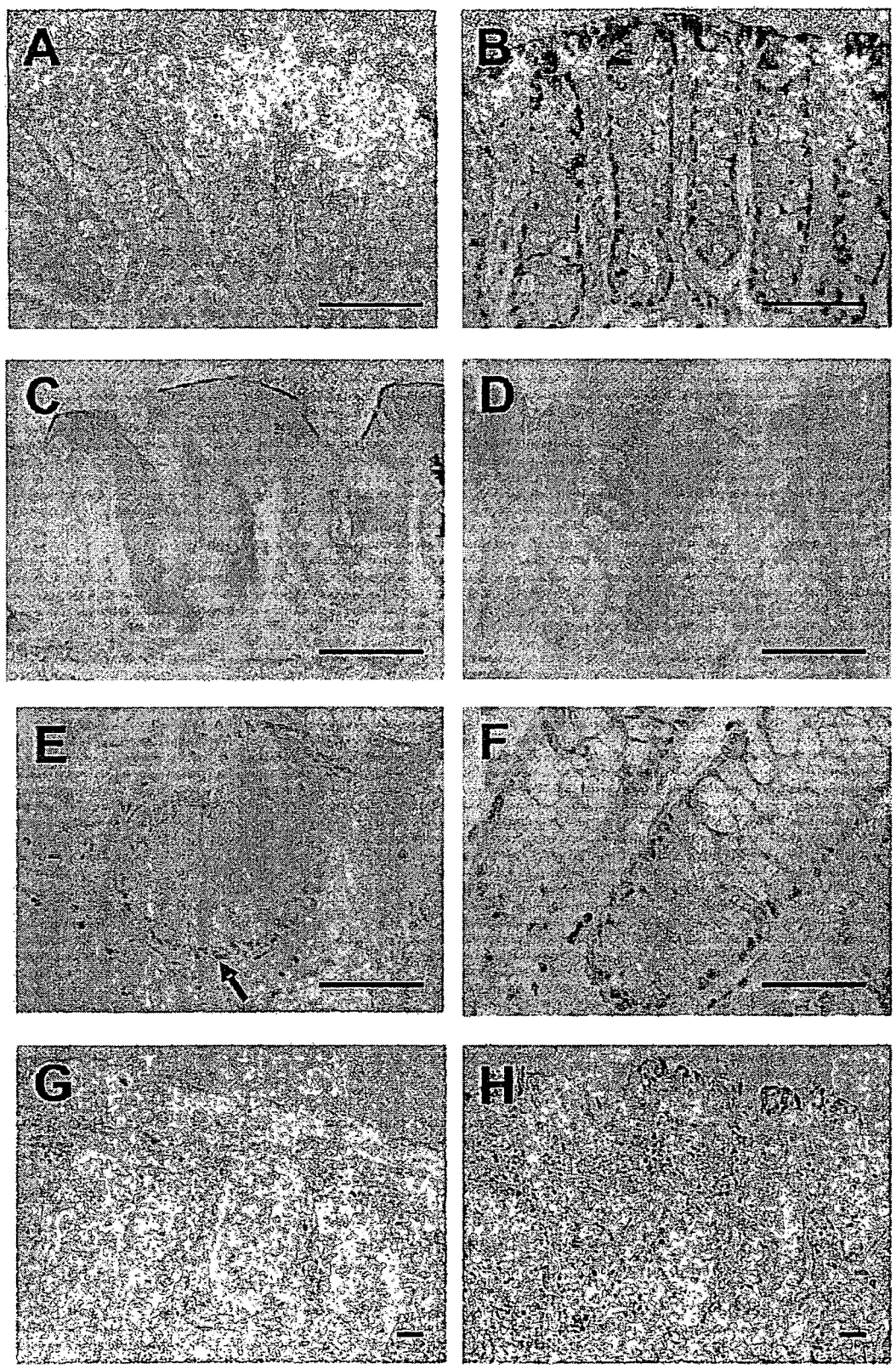
FIG. 2, panels A-H, depict a shift to less differentiated colon epithelium in a mouse H19 DMR mutation model and in colonoscopy clinic patients with LOI.

The sensitivity was reduced but the specificity increased when musashi1 staining was combined with a second marker, twist: increased staining was seen in 6 of 11 patients with LOI, compared with 1 of 14 patients without LOI (P=0.02, Fisher exact test) (FIG. 2, panel G through H). While twist staining alone did not achieve statistical significance (P=0.07), the two markers were non-overlapping, suggesting heterogeneity in downstream effects of LOI.

Cellular mechanisms by which epigenetic alterations in normal cells affect cancer risk are discussed herein. The mechanisms effectively alter the balance of differentiated and undifferentiated cells. The epigenetically-mediated shift in normal tissue to a more undifferentiated state, as described here, may increase the target cell population for subsequent genetic alterations, or may act alone in tumor initiation. In LOI-mediated Wilms tumor in the rare disorder Beckwith-Wiedemann syndrome (BWS), tumors arise because of an expanded population of nephrogenic precursor cells (Beckwith, et al., Peatr. Pathol. 10, 1 (1990)). Interestingly, we observed pancreatic islet cell hyperplasia, a feature of BWS, in LOI(+) Min mice (data not shown), suggesting that LOI may also predispose to the development of other tumor types. Genetic mechanisms altering cell differentiation and/or disrupting crypt architecture have been described (Haramis et al., Science 303, 1684 (2004); van de Wetering et al., Cell 111, 241 (2002); Yang, et al., Cancer Res. 63, 4990 (2003); Velcich et al., Science 295, 1726 (2002)), although these mechanisms are not common in normal human tissue.

Mice and genotyping: H19 mutant mice with C57BL/6J background carrying a deletion in the structural H19 gene (3 kb) and 10 kb of 5' flanking sequence were obtained. Paternal H19 heterozygotes were maintained without LOI phenotype by breeding female wild-type C57BL/6J and male H19+/−. Experimental crosses were performed between female H19+/− and male Apc+/Min (C57BL/6J). Mice were genotyped as follows using DNA extracted from the tails with DNeasy Tissue Kit (Qiagen, Valencia, Calif.). For H119, PCR was performed using two forward primers and one common reverse primer to obtain a 847-bp product for wild type allele and a 1,000-bp product for mutant allele. Primer sequences and annealing temperatures were: H19-F, TCC CCT CGC CTA GTC TGG AAG CA (SEQ ID NO:33); Mutant-F, GAA CTG TTC GCC AGG CTC AAG (SEQ ID NO:34); Common-R, ACA GCA GAC AGC AAG GGG AGG GT (SEQ ID NO:35); 66° C. For Apc, PCR and direct sequencing were performed using the following primers: Apc-F, TTT TGA CGC CAA TCG ACA T (SEQ ID NO:36); Apc-R, GGA ACT CGG TGG TAG AAG CA (SEQ ID NO:37); 55° C. Mice were sacrificed at 42 days and 120 days for tumor quantitation, histology, and immunostaining, and the entire intestine and other organs were collected. In addition, 150 day old H19 mutant mice carrying knock-in alleles of sequence change from GTGG to ATAT in three of the four CTCF target sites within H19 imprinting control region were established previously and crossed with SD7 mice as described. We compared paternally transmitted mutant alleles (non-LOI) to maternally transmitted alleles (LOI) with immunostaining performed on the same slide. All the animal experiments were performed in accordance with University guidelines.

Tumor analysis and immunostaining: For analysis of numbers and sizes of tumors, the entire intestine was flushed with cold PBS and was opened longitudinally. One half was frozen for further molecular analysis. The other half was fixed with 10% formalin and stained with 0.03% methylene blue, and numbers and sizes of tumors were measured under light microscopy, blinded for genotype.

For histopathological analysis, the entire intestine and other organs were fixed in 4% paraformaldehyde followed by 70% ethanol, and embedded in paraffin. H&E staining and immunohistochemistry against musashi1 (Chemicon, AB5977, 1:200 dilution), twist (Santa Cruz Biotechnology, SC-15393, 1:100 dilution), villin (Chemicon, MAB1671, 1:100 dilution), ephrin-B1 (R&D Systems, AF473, 1:25 dilution) and PCNA (Transduction, P56720 1:200 dilution) were performed comparing 4 mice in each group over the entire length of the small intestine, to analyze basic morphology, the balance of undifferentiated to differentiated compartments, the proliferation index, and the distribution of proliferative cells. Crypt length was measured from the base of intestinal crypts to the base of intestinal villi. Determinations of crypt length were blinded to genotype and based on a minimum of 5 individual measurements of random, well oriented sections of intestine on each of 2 different histologic sections (10 sections apart), defined as an area with a minimum of three adjacent villi and associated crypts cut perpendicularly to the long axis of the bowel lumen. Mushashi1 positive cells were counted using a hemocytometer in 10 individual crypts per mouse that were perpendicularly oriented to the long axis of the intestine. Quantitative image analysis of PCNA labeling was performed using the ACIS II automated image analysis system (Chromavision, San Juan Capistrano, Calif.) with measurements of both the percent and intensity of positive labeling cells determined in 10 individual crypts per mouse that were perpendicularly oriented to the long axis of the intestine. The distribution of proliferative cells was determined using a modification of the method described by Lipkin et al. using a hemocytometer to measure the height of the highest PCNA positive cell within an intestinal crypt divided by the overall height of that same crypt, again among 10 individual crypts per mouse. Measurements were expressed as a ratio, and the mean ratio for LOI(+) and LOI(−) mice was determined. For determinations of apoptotic rate, sections of the small intestine were evaluated for the number of positive labelling cells within a total of 20 intestinal crypts per mouse using a TUNEL Apoptotic Detection Kit (Upstate, Lake Placid, N.Y.).

The normal colonic mucosa of colonoscopy clinic patients with and without LOI were analyzed with immunostaining of musashi1 and twist. Musashi1 and twist immunolabeling was evaluated independently and blindly within the bottom half of intestinal crypts, the upper half of intestinal crypts and surface epithelium. Positive labeling was scored as nuclear staining with or without cytoplasmic staining in epithelial cells. RNA and protein analysis: Total RNA was extracted from tumor and non-tumor regions of the frozen intestine using RNeasy Kit with DNase I treatment (Qiagen), and reverse-transcribed using SuperScript II (Invitrogen, Carlsbad, Calif.). Expression level of Igf2 was quantified by real-time RT-PCR using SYBR Green PCR Core Reagents and ABI Prism 7700 Sequence Detection System (Applied Biosystems, San Jose, Calif.), and normalized to that of β-actin. Primers and annealing temperatures are as follows. Igf2: CAT CGT GGA AGA GTG CTG CT (SEQ ID NO:38) and GGG TAT CTG GGG AAG TCG T (SEQ ID NO:39), 60° C. β-actin: TAC CAC CAT GTA CCC AGG CA (SEQ ID NO:40) and GGA GGA GCA ATG ATC TTG AT (SEQ ID NO:41), 60° C.

Homogenized samples of small intestine of 42 day mice were applied to SDS-polyacrylamide gel (16%) electrophoresis with NuPAGE LDS buffer (Invitrogen) after acidification in 1 M acetic acid and lyophilization. Gels were transferred onto Immune-Blot PVDF membrane (BioRad, Hercules, Calif.), and the membranes were blocked with blocking buffer (5% non-fat dried milk, 0.1% Tween-20 in TBS) at 4° C. overnight, incubated with a 1:500 dilution of Igf2 antibody (Upstate, Lake Placid, N.Y.) or a 1:1000 dilution of Igf2 antibody (Abcam, Cambridge, Mass.) at room temperature for 1 h. After treatment with HRP conjugated secondary antibody and ECL detection reagents (Amersham, Piscataway, N.J.), and exposure to X-ray film, signal intensities were measured with a scanning densitometer. The gels were stained with SimplyBlue SafeStain (Invitrogen), and the intensities of the staining were measured with a scanning densitometer to correct the signal intensities.

TABLE 1

Increased adenoma number and surface area in LOI(+) Min mice. Displayed are the adenoma counts, as well as counts corrected for intestinal surface area alone, or for both intestinal and adenoma surface area.

| Genotype | N | Small intestine | Fold increase; P value | Colon | Fold increase; P value |
|---|---|---|---|---|---|
| Number of adenomas | | | | | |
| LOI(−) Min | 81 | 27.7 ± 1.3 | 2.2; | 1.3 ± 0.1 | 2.2; |
| LOI(+) Min | 59 | 60.4 ± 3.7 | <0.00001 | 2.9 ± 0.3 | <0.0001 |
| Surface area of adenomas (% of intestine occupied by adenomas) | | | | | |
| LOI(−) Min | 81 | 2.2 ± 0.1 | 2.4; | 2.3 ± 0.3 | 2.5; |
| LOI(+) Min | 59 | 5.5 ± 0.4 | <0.00001 | 5.8 ± 0.9 | <0.001 |
| Number of adenomas/10 $cm^2$ of intestine | | | | | |
| LOI(−) Min | 81 | 10.8 ± 0.5 | 1.8; | 3.7 ± 0.5 | 1.9; |
| LOI(+) Min | 59 | 19.2 ± 1.1 | <0.00001 | 7.0 ± 0.8 | <0.0001 |

Mean ± standard error (SE);
P value was calculated by t-test.

TABLE 2

Semi-quantitative analysis of musashi1 staining in intestinal crypts. The number of Mushashi1-positive cells was analyzed in LOI(−) Min mice and LOI(+) Min mice, and the number of crypts containing ≥6 and <6 Musashi1 positive cells is shown. P value was calculated by Fisher exact test.

| | Number of crypts | | |
|---|---|---|---|
| Genotypes | ≥6 musashi1(+) cells | <6 musashi1(+) cells | P value |
| LOI(−) Min | 5 | 35 | <0.01 |
| LOI(+) Min | 17 | 23 | |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining predisposition of a subject to developing colorectal cancer comprising:
   a) detecting at least one biomarker in undifferentiated cells and differentiated cells of a colorectal tissue sample from the subject, the at least one biomarker comprising Musashi 1 (Msi1);
   b) calculating a ratio of undifferentiated to differentiated cells in the sample from the subject by identifying and quantitating via computerized analysis the at least one biomarker;
   c) performing statistical analysis via a computerized algorithm to compare the ratio of undifferentiated to differentiated cells to a normal reference ratio;
   d) determining a predisposition of the subject to develop colorectal cancer by detecting an increase in the ratio of undifferentiated to differentiated cells, as compared to the normal reference ratio, the increase being indicative of a predisposition for developing colorectal cancer;
   e) storing the comparison on a computer readable medium; and
   f) isolating a cell displaying abnormal expression of a target gene that directly or indirectly results from loss of imprinting and analyzing methylation status of the target gene, wherein analyzing comprises a bisulfite treatment of the target gene.

2. The method of claim 1, wherein the target gene is selected from H19 or IGF2.

3. The method of claim 1, wherein the target gene is selected from the group consisting of Igf1R, IRS-1, IRS-2, PI3K, Akt, p70S6 kinase, FOXO, GSK3, MDM2, mTOR, Cyclin D1, c-Myc, Shc, Grb2, SOS, Ras, Raf, MEK, Erk, and MAPK gene.

4. The method of claim 1, wherein the change in methylation is hypomethylation.

5. The method of claim 4, wherein the method comprises analyzing the Biological sample for hypomethylation of both a DMR of the H19 gene and a DMR of the IGF2 gene.

6. The method of claim 2, wherein the reference ratio is generated from tissue obtained from a subject comprising cells displaying normal imprinting of at least one of the H19 gene and the IGF2 gene.

7. The method of claim 1, wherein the at least one biomarker further comprises Shh (Sonic hedgehog), Tcf4, Lef1, Twist, EphB2, EphB3, Hes1, Notch1, Hoxa9, Dkk1, Tle6, Tcf3, Bmi1, Kit, Cdx1, Hes5, Oct4, Ki-67, β-catenin, Noggin, BMP4, PTEN (phosphorylated PTEN), Akt (phosphorylated Akt), Villin, Aminopeptidase N (anpep), Sucrase isomaltase (SI), Ephrin-B1 (EfnB1), Cdx2, Crip, Apoa1, Aldh1b1, Calb3, Dgat1, Dgat2, Clu, Hephaestin, Gas1, Ihh (Indian hedgehog), Intrinsic factor B12 receptor, IFABP, and KLF4 or combination thereof.

8. The method of claim 1, wherein determining the ratio of undifferentiated to differentiated cells in the sample comprises:
   a) imaging the sample using immunohistochemical identification of the at least one biomarker;
   b) imaging the sample using standard microscopy and distinguishing differentiated from undifferentiated cells using morphologic measurements;
   c) imaging the sample using immunohistochemical identification of proliferation antigens and their distribution within colonic crypts;
   d) imaging the sample using immunoflourescent identification of molecules specific to the at least one biomarker;
   e) measuring RNA levels;
   f) measuring gene expression;
   g) whole genome expression analyses; or
   h) allele specific expression.

9. The method of claim 1, wherein the cells are epithelial cells.

10. The method of claim 9, wherein the epithelial cells are obtained from a rectal Pap test.

11. The method of claim 9, wherein the epithelial cells are obtained from intestinal tissue.

12. The method of claim 11, wherein the intestinal tissue is obtained from the colon.

13. The method of claim 11, wherein the epithelial cells are obtained from the lumen of the intestinal tissue.

14. The method of claim 13, wherein the epithelial cells are obtained from the crypts of the lumen.

15. The method of claim 1, wherein the subject is not previously known to have a colorectal neoplasm.

16. The method of claim 1, further comprising correlating the ratio derived from the subject with the subject's family genetic history.

17. The method of claim 1, wherein the subject is subjected to additional tests selected from the group consisting of chest X-rays, colorectal examinations, endoscopic examination, MRI, CAT scanning, gallium scanning, and barium imaging.

18. The method of claim 1, wherein the subject is a human.

* * * * *

SEQUENCE LISTING

```
<160> NUMBER OF SEQ ID NOS: 41

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
ggtgaggatg ggtttttgtt                                               20

<210> SEQ ID NO 2
<211> LENGTH: 21
<212> TYPE: DNA
<213> ORGANISM: Artificial sequence
<220> FEATURE:
<223> OTHER INFORMATION: Primer

<400> SEQUENCE: 2
ctactctccc aacctcccta a                                             21

<210> SEQ ID NO 3
<211> LENGTH: 20
<212> TYPE: DNA
<213> ORGANISM: Artificial sequence
```

```
<220> FEATURE:
<223> OTHER INFORMATION: Primer

<400> SEQUENCE: 3 attggggtg gagggtgtat                                                    20

<210> SEQ ID NO 4
<211> LENGTH: 21
<212> TYPE: DNA
<213> ORGANISM: Artificial sequence
<220> FEATURE:
<223> OTHER INFORMATION: Primer

<400> SEQUENCE: 4
tctattacac cctaaaccca a                                                 21

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5
atcttgctga cctcaccaag g                                                 21

<210> SEQ ID NO 6
<211> LENGTH: 21
<212> TYPE: DNA
<213> ORGANISM: Artificial sequence
<220> FEATURE:
<223> OTHER INFORMATION: Primer

<400> SEQUENCE: 6
cgatacgaag acgtggtgtg g                                                 21

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
ccgactaagg acagccccca aa                                                22

<210> SEQ ID NO 8
<211> LENGTH: 22
<212> TYPE: DNA
<213> ORGANISM: Artificial sequence
<220> FEATURE:
<223> OTHER INFORMATION: Primer

<400> SEQUENCE: 8
tggaagtctc tgctctcctg tc                                                22

<210> SEQ ID NO 9
<211> LENGTH: 22
<212> TYPE: DNA
<213> ORGANISM: Artificial sequence
<220> FEATURE:
<223> OTHER INFORMATION: Primer

<400> SEQUENCE: 9
acagtgttcc tggagtctcg ct                                                22
```

```
<210> SEQ ID NO 10
<211> LENGTH: 22
<212> TYPE: DNA
<213> ORGANISM: Artificial sequence
<220> FEATURE:
<223> OTHER INFORMATION: Primer

<400> SEQUENCE: 10
cacttccgat tccacagcta ca                                              22

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
acagggtctc tggcaggctc aa                                              22

<210> SEQ ID NO 12
<211> LENGTH: 22
<212> TYPE: DNA
<213> ORGANISM: Artificial sequence
<220> FEATURE:
<223> OTHER INFORMATION: Primer

<400> SEQUENCE: 12
atgagtgtcc tattcccaga tg                                              22

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
aactggggtt cgcccgtgga a                                               21

<210> SEQ ID NO 14
<211> LENGTH: 21
<212> TYPE: DNA
<213> ORGANISM: Artificial sequence
<220> FEATURE:
<223> OTHER INFORMATION: Primer

<400> SEQUENCE: 14
caaattcacc tctccacgtg c                                               21

<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15
gatcctgatg gggttaggat gt                                              22

<210> SEQ ID NO 16
<211> LENGTH: 22
<212> TYPE: DNA
<213> ORGANISM: Artificial sequence
<220> FEATURE:
<223> OTHER INFORMATION: Primer
```

```
<400> SEQUENCE: 16
ggaatttcca tggcatgaaa at                                          22

<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
ggtctgcctt ggtctcctaa ct                                          22

<210> SEQ ID NO 18
<211> LENGTH: 22
<212> TYPE: DNA
<213> ORGANISM: Artificial sequence
<220> FEATURE:
<223> OTHER INFORMATION: Primer

<400> SEQUENCE: 18
ggccactttc ctgtctgaag ac                                          22

<210> SEQ ID NO 19
<211> LENGTH: 22
<212> TYPE: DNA
<213> ORGANISM: Artificial sequence
<220> FEATURE:
<223> OTHER INFORMATION: Primer

<400> SEQUENCE: 19
cagtctccac tccactccca ac                                          22

<210> SEQ ID NO 20
<211> LENGTH: 22
<212> TYPE: DNA
<213> ORGANISM: Artificial sequence
<220> FEATURE:
<223> OTHER INFORMATION: Primer

<400> SEQUENCE: 20
gacctctccc tcccagacca ct                                          22

<210> SEQ ID NO 21
<211> LENGTH: 25
<212> TYPE: DNA
<213> ORGANISM: Artificial sequence
<220> FEATURE:
<223> OTHER INFORMATION: Primer

<400> SEQUENCE: 21
gagtttgggg gttttttgtat agtat                                      25

<210> SEQ ID NO 22
<211> LENGTH: 24
<212> TYPE: DNA
<213> ORGANISM: Artificial sequence
<220> FEATURE:
<223> OTHER INFORMATION: Primer

<400> SEQUENCE: 22
cttaaatccc aaaccataac acta                                        24
```

<210> SEQ ID NO 23
<211> LENGTH: 23
<212> TYPE: DNA
<213> ORGANISM: Artificial sequence
<220> FEATURE:
<223> OTHER INFORMATION: Primer

<400> SEQUENCE: 23
gtatatgggt atttttttgga ggt                                           23

<210> SEQ ID NO 24
<211> LENGTH: 21
<212> TYPE: DNA
<213> ORGANISM: Artificial sequence
<220> FEATURE:
<223> OTHER INFORMATION: Primer

<400> SEQUENCE: 24
ccataacact aaaaccctca a                                              21

<210> SEQ ID NO 25
<211> LENGTH: 24
<212> TYPE: DNA
<213> ORGANISM: Artificial sequence
<220> FEATURE:
<223> OTHER INFORMATION: Primer

<400> SEQUENCE: 25
gggaatgttt atttatgtat gaag                                           24

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
taaaaacctc ctccacctcc                                                20

<210> SEQ ID NO 27
<211> LENGTH: 21
<212> TYPE: DNA
<213> ORGANISM: Artificial
<220> FEATURE:
<223> OTHER INFORMATION: Primer

<400> SEQUENCE: 27
taatttattt agggtggtgt t                                              21

<210> SEQ ID NO 28
<211> LENGTH: 20
<212> TYPE: DNA
<213> ORGANISM: Artificial sequence
<220> FEATURE:
<223> OTHER INFORMATION: Primer

<400> SEQUENCE: 28
tccaaacacc cccaccttaa                                                20

<210> SEQ ID NO 29
<211> LENGTH: 26
<212> TYPE: DNA
<213> ORGANISM: Artificial sequence
<220> FEATURE:
<223> OTHER INFORMATION: Primer

<400> SEQUENCE: 29
gtataggtat ttttggaggt ttttta                                           26

<210> SEQ ID NO 30
<211> LENGTH: 26
<212> TYPE: DNA
<213> ORGANISM: Artificial sequence
<220> FEATURE:
<223> OTHER INFORMATION: Primer

<400> SEQUENCE: 30
cctaaaataa atcaaacaca taaccc                                           26

<210> SEQ ID NO 31
<211> LENGTH: 23
<212> TYPE: DNA
<213> ORGANISM: Artificial sequence
<220> FEATURE:
<223> OTHER INFORMATION: Primer

<400> SEQUENCE: 31
gaggtttttt attttagttt tgg                                              23

<210> SEQ ID NO 32
<211> LENGTH: 22
<212> TYPE: DNA
<213> ORGANISM: Artificial sequence
<220> FEATURE:
<223> OTHER INFORMATION: Primer

<400> SEQUENCE: 32
actataatat ataaacctac ac                                               22

<210> SEQ ID NO 33
<211> LENGTH: 23
<212> TYPE: DNA
<213> ORGANISM: Artificial sequence
<220> FEATURE:
<223> OTHER INFORMATION: Primer

<400> SEQUENCE: 33
tcccctcgcc tagtctggaa gca                                              23

<210> SEQ ID NO 34
<211> LENGTH: 21
<212> TYPE: DNA
<213> ORGANISM: Artificial sequence
<220> FEATURE:
<223> OTHER INFORMATION: Primer

<400> SEQUENCE: 34
gaactgttcg ccaggctcaa g                                                21

<210> SEQ ID NO 35
<211> LENGTH: 23
<212> TYPE: DNA
<213> ORGANISM: Artificial sequence
<220> FEATURE:
<223> OTHER INFORMATION: Primer

<400> SEQUENCE: 35
acagcagaca gcaaggggag ggt                                              23

```
<210> SEQ ID NO 36
<211> LENGTH: 19
<212> TYPE: DNA
<213> ORGANISM: Artificial sequence
<220> FEATURE:
<223> OTHER INFORMATION: Primer

<400> SEQUENCE: 36
ttttgacgcc aatcgacat                                              19

<210> SEQ ID NO 37
<211> LENGTH: 20
<212> TYPE: DNA
<213> ORGANISM: Artificial sequence
<220> FEATURE:
<223> OTHER INFORMATION: Primer

<400> SEQUENCE: 37
ggaactcggt ggtagaagca                                             20

<210> SEQ ID NO 38
<211> LENGTH: 20
<212> TYPE: DNA
<213> ORGANISM: Artificial sequence
<220> FEATURE:
<223> OTHER INFORMATION: Primer

<400> SEQUENCE: 38
catcgtggaa gagtgctgct                                             20

<210> SEQ ID NO 39
<211> LENGTH: 19
<212> TYPE: DNA
<213> ORGANISM: Artificial sequence
<220> FEATURE:
<223> OTHER INFORMATION: Primer

<400> SEQUENCE: 39
gggtatctgg ggaagtcgt                                              19

<210> SEQ ID NO 40
<211> LENGTH: 20
<212> TYPE: DNA
<213> ORGANISM: Artificial sequence
<220> FEATURE:
<223> OTHER INFORMATION: Primer

<400> SEQUENCE: 40
taccaccatg tacccaggca                                             20

<210> SEQ ID NO 41
<211> LENGTH: 20
<212> TYPE: DNA
<213> ORGANISM: Artificial sequence
<220> FEATURE:
<223> OTHER INFORMATION: Primer

<400> SEQUENCE: 41
ggaggagcaa tgatcttgat                                             20
```